(12) United States Patent
Faustman

(10) Patent No.: US 6,284,879 B1
(45) Date of Patent: Sep. 4, 2001

(54) TRANSPORT ASSOCIATED PROTEIN SPLICE VARIANTS

(75) Inventor: Denise L. Faustman, Weston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/061,764

(22) Filed: Apr. 16, 1998

(51) Int. Cl.[7] ............................ C07H 21/04; C12N 15/11; C12N 15/63; C12N 15/85; C12P 21/00

(52) U.S. Cl. ................. 536/23.1; 435/320.1; 435/300; 435/350; 435/387.1; 435/70.1; 435/325; 514/44

(58) Field of Search ................. 536/23.1; 435/320.1, 435/70.1; 530/300, 350, 307.1; 514/44

(56) References Cited

U.S. PATENT DOCUMENTS

| | | |
|---|---|---|
| 4,946,778 | 8/1990 | Ladner ........................... 435/69.6 |
| 5,538,854 | 7/1996 | Faustman ........................... 435/6 |

OTHER PUBLICATIONS

Bahram et al. (1991) Proc. Natl. Acad. Sci. USA, vol. 88, 10094–10098, Nov. 1991.*
Wang et al. (1995) Human Gene Therapy, vol. 6, 1005–1017, Aug. 1995.*
Androlewicz et al., *Proc. Natl. Acad. Sci. USA*, 91(26): 12716–12720 (1994).
Attaya et al., *Nature*, 355:647 (1992).
Cole et al., *Monoclonal Antibodies and Cancer Therapy*, Alan R. Liss, Inc., pp. 77–96 (1985).
Daniel et al., *J. Immunol.*, 159: 2350–2357 (1997).
Faustman et al., *Science*, 254:1756–1761 (1991).
Fu et al., *J. Clin. Invest.*, 91:2301 (1993).
Hill et al., *Proc. Natl. Acad. Sci. USA*, 92: 341–343 ,(1995).
Howard., *Proc. Natl. Acad. Sci. USA*, 90: 3777–3779 (1993).
Kohler and Milstein, *Nature*, 256:495–497 (1975).
Kozbor et al., *Immunology Today*, 4:72 (1983).
Momburg et al., *Nature*, 367:648 (1994).
Momburg et al., *J. Exp. Med.*, 179:1613 (1994).
Neefjes et al., *Science*, 261:769 (1993).
Neefjes et al., *Eur. J. Immunol.*, 25:1133 (1995).
Obst et al., *Eur. J. Immunol.*, 25: 2170–2176 (1995).
Ortmann et al., *Nature*, 368:864 (1994).
Powis et al., *Immunogenetics*, 37:373–380 (1990).
Powis et al., *J. Exp. Med.*, 173:913 (1991).
Powis et al., *Nature*, 357:211–215 (1992).
Powis et al., *Immunity*, 4(2):159–165 (1996).
Schumacher et al., *Proc. Natl. Acad. Sci. USA*, 91(26):13004–13008 (1994).
Spies and DeMars, *Nature*, 351:323 (1991).

* cited by examiner

Primary Examiner—Deborah J. R. Clark
Assistant Examiner—Anne Marie S. Beckerleg
(74) *Attorney, Agent, or Firm*—Leon R. Yankwich; Kenneth P. Zwicker

(57) ABSTRACT

Splice variants of known TAP1 and TAP2 proteins, which are involved in translocation of antigen peptides into the endoplasmic reticulum for complexing with MHC class I molecules and eventual display on the cell surface, are disclosed. A fully sequenced and characterized splice variant of TAP2, designated TAP2iso, is shown to form functional heterodimers with TAP1 and to exhibit a peptide specificity that differs from previously studied TAP1/TAP2 transporter proteins. The discovery of splice variant TAP subunits alters the prior theory of immune response and introduces a mechanism for diversification of antigen display to the CD8-positive T cells of the immune system. Methods for diagnosis and treatment of diseases or conditions associated with abnormal TAP splice variant expression, or of expanding the repertoire of antigen peptides to which an individual's immune system is capable of responding, are also disclosed.

12 Claims, 15 Drawing Sheets

```
TAP1iso:   TAGTTTCATC  TCTGGACTCC  CTCAGGGCTA  TGACACAGGT  AGACGAGGCT  GGGAGCCAGC
TAP1iso2:  TAGTTTCATC  TCTGGACTCC  CTCAGGGCTA  TGACACAGGT  AGACGAGGCT  GGGAGCCAGC TAP1iso:   TGTCAGGGGG  TCAGCGACAG  GCAGTGGCGT  TGGCCCGAGC  ATTGATCCGG  AAACCGTGTG
TAP1iso2:  TGTCAGGGGG  TCAGCGACAG  GCAGTGGCGT  TGGCCCGAGC  ATTGATCCGG  AAACCGTGTG TAP1iso:   TACTTATCCT  GGATGATGCC  ACCAGTGCCC  TGGATGCAAA  CAGCCAGTTA  CAGGTGAGGC
TAP1iso2:  TACTTATCCT  GGATGATGCC  ACCAGTGCCC  TGGATGCAAA  CAGCCAGTTA  CAG///////

TAP1iso:   AGTCATCTTC  TTAATGGCTA  TATCCCACCC  AATCTTGCTT  CTTTTATACA  TCTTCTGTTA
TAP1iso2:  //////////  //////////  //////////  //////////  //////////  //////////

TAP1iso:   GTTTTACTAA  CATCATAATT  ATACAAACCA  GTCCTTGCAG  TTCTCAGTTC  CCAAATCCAG
TAP1iso2:  //////////  //////////  //////////  GTCCTTGCAG  TTCTCAGTTC  CCAAATCCAG TAP1iso:   TTCCATTGGA  TGCCTCCCCA  AGGAGTAGAG  ATAGAAGACG  AGGCAAAGAC  ACCT
TAP1iso2:  TTCCATTGGA  TGCCTCCCCA  AGGAGTAGAG  ATAGAAGACG  AGGCAAAGAC  ACCT
```

FIG. 9A

SEQUENCE LISTING (1) GENERAL INFORMATION:

(iii) NUMBER OF SEQUENCES: 23

(2) INFORMATION FOR SEQ ID NO: 1:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 1:

Lys Thr Leu Trp Lys Phe Met Ile Phe
 1              5

(2) INFORMATION FOR SEQ ID NO: 2:

(i) SEQUENCE CHARACTERISTICS:
        (A) LENGTH: 653 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 2:

Met Arg Leu Pro Asp Leu Arg Pro Trp Thr Ser Leu Leu Val Asp
 1         5              10            15

Ala Ala Leu Leu Trp Leu Leu Gln Gly Pro Leu Gly Thr Leu Leu Pro

```
                   20                  25                  30
Gln Gly Leu Pro Gly Leu Trp Leu Glu Gly Thr Leu Arg Leu Gly Gly
            35                  40                  45

Leu Trp Gly Leu Leu Lys Leu Arg Gly Leu Leu Gly Phe Val Gly Thr
 50                  55                  60

Leu Leu Leu Pro Leu Cys Leu Ala Thr Pro Leu Thr Val Ser Leu Arg
 65                  70                  75                  80

Ala Leu Val Ala Gly Ala Ser Arg Ala Pro Ala Arg Val Ala Ser
                 85                  90                  95

Ala Pro Trp Ser Trp Leu Leu Val Gly Tyr Ala Ala Gly Leu Ser
             100                 105                 110

Trp Ser Leu Trp Ala Val Leu Ser Pro Pro Gly Ala Gln Glu Lys Glu
         115                 120                 125

Gln Asp Gln Val Asn Asn Lys Val Leu Met Trp Arg Leu Leu Lys Leu
    130                 135                 140

Ser Arg Pro Asp Leu Pro Leu Val Ala Ala Phe Phe Phe Leu Val
145                 150                 155                 160

Leu Ala Val Leu Gly Glu Thr Leu Ile Pro His Tyr Ser Gly Arg Val
                165                 170                 175

Ile Asp Ile Leu Gly Gly Asp Phe Asp Pro His Ala Phe Ala Ser Ala
            180                 185                 190

Ile Phe Phe Met Cys Leu Phe Ser Phe Gly Ser Ser Leu Ser Ala Gly
        195                 200                 205

Cys Arg Gly Gly Cys Phe Thr Tyr Thr Met Ser Arg Ile Asn Leu Arg
    210                 215                 220

Ile Arg Glu Gln Leu Phe Ser Ser Leu Leu Arg Gln Asp Leu Gly Phe
225                 230                 235                 240

Phe Gln Glu Thr Lys Thr Gly Glu Leu Asn Ser Arg Leu Ser Ser Asp
                245                 250                 255

Thr Thr Leu Met Ser Asn Trp Leu Pro Leu Asn Ala Asn Val Leu Leu
            260                 265                 270

Arg Ser Leu Val Lys Val Val Gly Leu Tyr Gly Phe Met Leu Ser Ile
        275                 280                 285

Ser Pro Arg Leu Thr Leu Leu Ser Leu Leu His Met Pro Phe Thr Ile
    290                 295                 300

Ala Ala Glu Lys Val Tyr Asn Thr Arg His Gln Glu Val Leu Arg Glu
305                 310                 315                 320

Ile Gln Asp Ala Val Ala Arg Ala Gly Gln Val Val Arg Glu Ala Val
                325                 330                 335

Gly Gly Leu Gln Thr Val Arg Ser Phe Gly Ala Glu Glu His Glu Val
            340                 345                 350

Cys Arg Tyr Lys Glu Ala Lys Glu Gln Cys Arg Gln Leu Tyr Trp Arg
        355                 360                 365

Arg Asp Leu Glu Arg Ala Leu Tyr Leu Leu Ile Arg Arg Val Leu His
    370                 375                 380

Leu Gly Val Gln Met Leu Met Leu Ser Cys Gly Leu Gln Gln Met Gln
385                 390                 395                 400

Asp Gly Glu Leu Thr Gln Gly Ser Leu Leu Ser Phe Met Ile Tyr Gln
                405                 410                 415

Glu Ser Val Gly Ser Tyr Val Gln Thr Leu Val Tyr Ile Tyr Gly Asp
            420                 425                 430

Met Leu Ser Asn Val Gly Ala Ala Glu Lys Val Phe Ser Tyr Met Asp
        435                 440                 445
```

```
Arg Gln Pro Asn Leu Pro Ser Pro Gly Thr Leu Ala Pro Thr Thr Leu
    450                 455                 460

Gln Gly Val Val Lys Phe Gln Asp Val Ser Phe Ala Tyr Pro Asn Arg
465                 470                 475                 480

Pro Asp Arg Pro Val Leu Lys Gly Leu Thr Phe Thr Leu Arg Pro Gly
                485                 490                 495

Glu Val Thr Ala Leu Val Gly Pro Asn Gly Ser Gly Lys Ser Thr Val
                500                 505                 510

Ala Ala Leu Leu Gln Asn Leu Tyr Gln Pro Thr Gly Gly Gln Val Leu
            515                 520                 525

Leu Asp Glu Lys Pro Ile Ser Gln Tyr Glu His Cys Tyr Leu His Ser
530                 535                 540

Gln Val Val Ser Val Gly Gln Glu Pro Val Leu Phe Ser Gly Ser Val
545                 550                 555                 560

Arg Asn Asn Ile Ala Tyr Gly Leu Gln Ser Cys Glu Asp Asp Lys Val
                565                 570                 575

Met Ala Ala Gln Ala Ala His Ala Asp Asp Phe Ile Gln Glu Met
            580                 585                 590

Glu His Gly Ile Tyr Thr Asp Val Gly Glu Lys Gly Ser Gln Leu Ala
            595                 600                 605

Ala Gly Gln Lys Gln Arg Leu Ala Ile Ala Arg Ala Leu Val Arg Asp
610                 615                 620

Pro Arg Val Leu Ile Leu Asp Glu Ala Thr Ser Ala Leu Asp Val Gln
625                 630                 635                 640

Cys Glu Gln Ala Lys Thr Leu Trp Lys Phe Met Ile Phe
                645                 650

(2) INFORMATION FOR SEQ ID NO: 3:

(i) SEQUENCE CHARACTERISTICS:
        (A) LENGTH: 19 bases
        (B) TYPE: nucleic acid
        (C) STRANDEDNESS: single
        (D) TOPOLOGY: linear (ii) MOLECULE TYPE: other nucleic acid
        (A) DESCRIPTION: synthetic DNA fragment (xi) SEQUENCE DESCRIPTION: SEQ ID NO: 3:

ATGTAGGGGA GAAGGGAAG                                              19

(2) INFORMATION FOR SEQ ID NO: 4:

(i) SEQUENCE CHARACTERISTICS:
        (A) LENGTH: 1959 bases
        (B) TYPE: nucleic acid
        (C) STRANDEDNESS: single
        (D) TOPOLOGY: linear (ii) MOLECULE TYPE: other nucleic acid
        (A) DESCRIPTION: synthetic DNA fragment (xi) SEQUENCE DESCRIPTION: SEQ ID NO: 4:

ATGCGGCTCC CTGACCTGAG ACCCTGGACC TCCCTGCTGC TGGTGGACGC             50

GGCTTTACTG TGGCTGCTTC AGGGCCCTCT GGGGACTTTG CTTCCTCAAG            100

GGCTGCCAGG ACTATGGCTG GAGGGGACCC TGCGGCTGGG AGGGCTGTGG            150

GGGCTGCTAA AGCTAAGAGG GCTGCTGGGA TTTGTGGGGA CACTGCTGCT            200

CCCGCTCTGT CTGGCCACCC CCCTGACTGT CTCCCTGAGA GCCCTGGTCG            250
```

```
CGGGGGCCTC ACGTGCTCCC CCAGCCAGAG TCGCTTCAGC CCCTTGGAGC        300

TGGCTGCTGG TGGGGTACGG GGCTGCGGGG CTCAGCTGGT CACTGTGGGC        350

TGTTCTGAGC CCTCCTGGAG CCCAGGAGAA GGAGCAGGAC CAGGTGAACA        400

ACAAAGTCTT GATGTGGAGG CTGCTGAAGC TCTCCAGGCC GGACCTGCCT        450

CTCCTCGTTG CCGCCTTCTT CTTCCTTGTC CTTGCTGTTT TGGGTGAGAC        500

ATTAATCCCT CACTATTCTG GTCGTGTCAT TGACATCCTG GGAGGTGATT        550

TTGACCCCCA TGCCTTTGCC AGTGCCATCT TCTTCATGTG CCTCTTCTCC        600

TTTGGCAGCT CACTGTCTGC AGGCTGCCGA GGAGGCTGCT TCACCTACAC        650

CATGTCTCGA ATCAACTTGC GGATCCGGGA GCAGCTTTTC TCCTCCCTGC        700

TGCGCCAGGA CCTCGGTTTC TTCCAGGAGA CTAAGACAGG GGAGCTGAAC        750

TCACGGCTGA GCTCGGATAC CACCCTGATG AGTAACTGGC TTCCTTTAAA        800

TGCCAATGTG CTCTTGCGAA GCCTGGTGAA AGTGGTGGGG CTGTATGGCT        850

TCATGCTCAG CATATCGCCT CGACTCACCC TCCTTTCTCT GCTGCACATG        900

CCCTTCACAA TAGCAGCGGA GAAGGTGTAC AACACCCGCC ATCAGGAAGT        950

GCTTCGGAG ATCCAGGATG CAGTGGCCAG GGCGGGGCAG GTGGTGCGGG        1000

AAGCCGTTGG AGGGCTGCAG ACCGTTCGCA GTTTTGGGGC CGAGGAGCAT        1050

GAAGTCTGTC GCTATAAAGA GGCCCTTGAA CAATGTCGGC AGCTGTATTG        1100

GCGGAGAGAC CTGGAACGCG CCTTGTACCT GCTCATAAGG AGGGTGCTGC        1150

ACTTGGGTGT GCAGATGCTG ATGCTGAGCT GTGGGCTGCA GCAGATGCAG        1200

GATGGGGAGC TCACCCAGGG CAGCCTGCTT TCCTTTATGA TCTACCAGGA        1250

GAGCGTGGGG AGCTATGTGC AGACCCTGGT ATACATATAT GGGGATATGC        1300

TCAGCAACGT GGGAGCTGCA GAGAAGGTTT TCTCCTACAT GGACCGACAG        1350

CCAAATCTGC CTTCACCTGG CACGCTTGCC CCCACCACTC TGCAGGGGGT        1400

TGTGAAATTC CAAGACGTCT CCTTTGCATA TCCCAATCGC CCTGACAGGC        1450

CTGTGCTCAA GGGGCTGACG TTTACCCTAC GTCCTGGTGA GGTGACGGCG        1500

CTGGTGGGAC CCAATGGGTC TGGGAAGAGC ACAGTGGCTG CCCTGCTGCA        1550

GAATCTGTAC CAGCCCACAG GGGACAGGT GCTGCTGGAT GAAAAGCCCA        1600

TCTCACAGTA TGAACACTGC TACCTGCACA GCCAGGTGGT TTCAGTTGGG        1650

CAGGAGCCTG TGCTGTTCTC CGGTTCTGTG AGGAACAACA TTGCTTATGG        1700

GCTGCAGAGC TGCGAAGATG ATAAGGTGAT GGCGGCTGCC CAGGCTGCCC        1750

ACGCAGATGA CTTCATCCAG GAAATGGAGC ATGAATATA CACAGATGTA        1800

GGGGAGAAGG GAAGCCAGCT GGCTGCGGGA CAGAAACAAC GTCTGGCCAT        1850

TGCCCGGGCC CTTGTACGAG ACCCGCGGGT CCTCATCCTG GATGAGGCTA        1900

CTAGTGCCCT AGATGTGCAG TGCGAGCAGG CCAAAACCCT TTGGAAGTTC        1950

ATGATATTT                                                     1959
```

(2) INFORMATION FOR SEQ ID NO: 5:

(i) SEQUENCE CHARACTERISTICS:
        (A) LENGTH: 27 bases
        (B) TYPE: nucleic acid
        (C) STRANDEDNESS: single
        (D) TOPOLOGY: linear

```
    (ii) MOLECULE TYPE: other nucleic acid
         (A) DESCRIPTION: synthetic DNA fragment (xi) SEQUENCE DESCRIPTION: SEQ ID NO: 5:

AAAACCCTTT GGAAGTTCAT GATATTT                                          27

(2) INFORMATION FOR SEQ ID NO: 6:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 6:

Arg Arg Tyr Gln Asn Ser Thr Glu Leu
 1               5

(2) INFORMATION FOR SEQ ID NO: 7:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 7:

Ile Tyr Leu Gly Pro Phe Ser Pro Asn Val Thr Leu
 1               5                  10

(2) INFORMATION FOR SEQ ID NO: 8:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 8:

Thr Val Asp Asn Lys Thr Arg Tyr Glu
 1               5

(2) INFORMATION FOR SEQ ID NO: 9:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 9:

Ser Tyr Ser Met Glu His Phe Arg Trp Gly Lys Pro Val Gly Lys Lys
 1               5                  10                  15

Arg Arg Pro Val Lys Val Tyr Pro
                20

(2) INFORMATION FOR SEQ ID NO: 10:

(i) SEQUENCE CHARACTERISTICS:
```

(A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 10:

Arg Gly Phe Phe Tyr Thr Pro Lys Ala
 1               5

(2) INFORMATION FOR SEQ ID NO: 11:

(i) SEQUENCE CHARACTERISTICS:
        (A) LENGTH: 25 bases
        (B) TYPE: nucleic acid
        (C) STRANDEDNESS: single
        (D) TOPOLOGY: linear (ii) MOLECULE TYPE: other nucleic acid
        (A) DESCRIPTION: synthetic DNA fragment (xi) SEQUENCE DESCRIPTION: SEQ ID NO: 11:

GTCCTGGAGA CGCCCCTGAG AAGAG                                              25

(2) INFORMATION FOR SEQ ID NO: 12:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: other nucleic acid
        (A) DESCRIPTION: synthetic DNA fragment (xi) SEQUENCE DESCRIPTION: SEQ ID NO: 12:

ATCCCACCTA GTGAGAATCC                                                    20

(2) INFORMATION FOR SEQ ID NO: 13:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: other nucleic acid
        (A) DESCRIPTION: synthetic DNA fragment (xi) SEQUENCE DESCRIPTION: SEQ ID NO: 13:

CATTCCTGAA GCTGACAGCA                                                    20

(2) INFORMATION FOR SEQ ID NO: 14:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: other nucleic acid
        (A) DESCRIPTION: synthetic DNA fragment (xi) SEQUENCE DESCRIPTION: SEQ ID NO: 14:

TTCAACCTCC ATGATGCTGC                                                    20

(2) INFORMATION FOR SEQ ID NO: 15:

(i) SEQUENCE CHARACTERISTICS:
    (A) LENGTH: 686 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO: 15:

```
Met Arg Leu Pro Asp Leu Arg Pro Trp Thr Ser Leu Leu Val Asp
 1               5                  10                  15

Ala Ala Leu Leu Trp Leu Leu Gln Gly Pro Leu Gly Thr Leu Leu Pro
             20                  25                  30

Gln Gly Leu Pro Gly Leu Trp Leu Glu Gly Thr Leu Arg Leu Gly Gly
         35                  40                  45

Leu Trp Gly Leu Leu Lys Leu Arg Gly Leu Leu Gly Phe Val Gly Thr
     50                  55                  60

Leu Leu Leu Pro Leu Cys Leu Ala Thr Pro Leu Thr Val Ser Leu Arg
 65                  70                  75                  80

Ala Leu Val Ala Gly Ala Ser Arg Ala Pro Pro Ala Arg Val Ala Ser
                 85                  90                  95

Ala Pro Trp Ser Trp Leu Leu Val Gly Tyr Gly Ala Ala Gly Leu Ser
            100                 105                 110

Trp Ser Leu Trp Ala Val Leu Ser Pro Pro Gly Ala Gln Glu Lys Glu
        115                 120                 125

Gln Asp Gln Val Asn Asn Lys Val Leu Met Trp Arg Leu Leu Lys Leu
    130                 135                 140

Ser Arg Pro Asp Leu Pro Leu Leu Val Ala Ala Phe Phe Leu Val
145                 150                 155                 160

Leu Ala Val Leu Gly Glu Thr Leu Ile Pro His Tyr Ser Gly Arg Val
                165                 170                 175

Ile Asp Ile Leu Gly Gly Asp Phe Asp Pro His Ala Phe Ala Ser Ala
            180                 185                 190

Ile Phe Phe Met Cys Leu Phe Ser Phe Gly Ser Ser Leu Ser Ala Gly
        195                 200                 205

Cys Arg Gly Gly Cys Phe Thr Tyr Thr Met Ser Arg Ile Asn Leu Arg
    210                 215                 220

Ile Arg Glu Gln Leu Phe Ser Ser Leu Leu Arg Gln Asp Leu Gly Phe
225                 230                 235                 240

Phe Gln Glu Thr Lys Thr Gly Glu Leu Asn Ser Arg Leu Ser Ser Asp
                245                 250                 255

Thr Thr Leu Met Ser Asn Trp Leu Pro Leu Asn Ala Asn Val Leu Leu
            260                 265                 270

Arg Ser Leu Val Lys Val Val Gly Leu Tyr Gly Phe Met Leu Ser Ile
        275                 280                 285

Ser Pro Arg Leu Thr Leu Leu Ser Leu Leu His Met Pro Phe Thr Ile
    290                 295                 300

Ala Ala Glu Lys Val Tyr Asn Thr Arg His Gln Glu Val Leu Arg Glu
305                 310                 315                 320

Ile Gln Asp Ala Val Ala Arg Ala Gly Gln Val Val Arg Glu Ala Val
                325                 330                 335

Gly Gly Leu Gln Thr Val Arg Ser Phe Gly Ala Glu Glu His Glu Val
            340                 345                 350

Cys Arg Tyr Lys Glu Ala Lys Glu Gln Cys Arg Gln Leu Tyr Trp Arg
        355                 360                 365
```

```
Arg Asp Leu Glu Arg Ala Leu Tyr Leu Leu Ile Arg Arg Val Leu His
    370                 375                 380

Leu Gly Val Gln Met Leu Met Leu Ser Cys Gly Leu Gln Gln Met Gln
385                 390                 395                 400

Asp Gly Glu Leu Thr Gln Gly Ser Leu Leu Ser Phe Met Ile Tyr Gln
                405                 410                 415

Glu Ser Val Gly Ser Tyr Val Gln Thr Leu Val Tyr Ile Tyr Gly Asp
                420                 425                 430

Met Leu Ser Asn Val Gly Ala Ala Glu Lys Val Phe Ser Tyr Met Asp
                435                 440                 445

Arg Gln Pro Asn Leu Pro Ser Pro Gly Thr Leu Ala Pro Thr Thr Leu
    450                 455                 460

Gln Gly Val Val Lys Phe Gln Asp Val Ser Phe Ala Tyr Pro Asn Arg
465                 470                 475                 480

Pro Asp Arg Pro Val Leu Lys Gly Leu Thr Phe Thr Leu Arg Pro Gly
                485                 490                 495

Glu Val Thr Ala Leu Val Gly Pro Asn Gly Ser Gly Lys Ser Thr Val
                500                 505                 510

Ala Ala Leu Leu Gln Asn Leu Tyr Gln Pro Thr Gly Gly Gln Val Leu
                515                 520                 525

Leu Asp Glu Lys Pro Ile Ser Gln Tyr Glu His Cys Tyr Leu His Ser
    530                 535                 540

Gln Val Val Ser Val Gly Gln Glu Pro Val Leu Phe Ser Gly Ser Val
545                 550                 555                 560

Arg Asn Asn Ile Ala Tyr Gly Leu Gln Ser Cys Glu Asp Asp Lys Val
                565                 570                 575

Met Ala Ala Ala Gln Ala Ala His Ala Asp Asp Phe Ile Gln Glu Met
                580                 585                 590

Glu His Gly Ile Tyr Thr Asp Val Gly Glu Lys Gly Ser Gln Leu Ala
                595                 600                 605

Ala Gly Gln Lys Gln Arg Leu Ala Ile Ala Arg Ala Leu Val Arg Asp
    610                 615                 620

Pro Arg Val Leu Ile Leu Asp Glu Ala Thr Ser Ala Leu Asp Val Gln
625                 630                 635                 640

Cys Glu Gln Ala Leu Gln Asp Trp Asn Ser Arg Gly Asp Arg Thr Val
                645                 650                 655

Leu Val Ile Ala His Arg Leu Gln Thr Val Gln Arg Ala His Gln Ile
                660                 665                 670

Leu Val Leu Gln Glu Gly Lys Leu Gln Lys Leu Ala Gln Leu
        675                 680                 685

(2) INFORMATION FOR SEQ ID NO: 16:

(i) SEQUENCE CHARACTERISTICS:
        (A) LENGTH: 42 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 16:

Leu Gln Asp Trp Asn Ser Arg Gly Asp Arg Thr Val Leu Val Ile Ala
                5                   10                  15

His Arg Leu Gln Thr Val Gln Arg Ala His Gln Ile Leu Val Leu Gln
                20                  25                  30
```

Glu Gly Lys Leu Gln Lys Leu Ala Gln Leu
         35                  40

(2) INFORMATION FOR SEQ ID NO: 17:

(i) SEQUENCE CHARACTERISTICS:
        (A) LENGTH: 2061 bases
        (B) TYPE: nucleic acid
        (C) STRANDEDNESS: single
        (D) TOPOLOGY: linear (ii) MOLECULE TYPE: other nucleic acid
        (A) DESCRIPTION: synthetic DNA fragment (xi) SEQUENCE DESCRIPTION: SEQ ID NO: 17:

```
ATGCGGCTCC CTGACCTGAG ACCCTGGACC TCCCTGCTGC TGGTGGACGC          50
GGCTTTACTG TGGCTGCTTC AGGGCCCTCT GGGGACTTTG CTTCCTCAAG         100
GGCTGCCAGG ACTATGGCTG GAGGGGACCC TGCGGCTGGG AGGGCTGTGG         150
GGGCTGCTAA AGCTAAGAGG GCTGCTGGGA TTTGTGGGGA CACTGCTGCT         200
CCCGCTCTGT CTGGCCACCC CCCTGACTGT CTCCCTGAGA GCCCTGGTCG         250
CGGGGGCCTC ACGTGCTCCC CCAGCCAGAG TCGCTTCAGC CCCTTGGAGC         300
TGGCTGCTGG TGGGGTACGG GGCTGCGGGG CTCAGCTGGT CACTGTGGGC         350
TGTTCTGAGC CCTCCTGGAG CCCAGGAGAA GGAGCAGGAC CAGGTGAACA         400
ACAAAGTCTT GATGTGGAGG CTGCTGAAGC TCTCCAGGCC GGACCTGCCT         450
CTCCTCGTTG CCGCCTTCTT CTTCCTTGTC CTTGCTGTTT TGGGTGAGAC         500
ATTAATCCCT CACTATTCTG GTCGTGTGAT TGACATCCTG GGAGGTGATT         550
TTGACCCCCA TGCCTTTGCC AGTGCCATCT TCTTCATGTG CCTCTTCTCC         600
TTTGGCAGCT CACTGTCTGC AGGCTGCCGA GGAGGCTGCT TCACCTACAC         650
CATGTCTCGA ATCAACTTGC GGATCCGGGA GCAGCTTTTC TCCTCCCTGC         700
TGCGCCAGGA CCTCGGTTTC TTCCAGGAGA CTAAGACAGG GGAGCTGAAC         750
TCACGGCTGA GCTCGGATAC CACCCTGATG AGTAACTGGC TTCCTTTAAA         800
TGCCAATGTG CTCTTGCGAA GCCTGGTGAA AGTGGTGGGG CTGTATGGCT         850
TCATGCTCAG CATATCGCCT CGACTCACCC TCCTTTCTCT GCTGCACATG         900
CCCTTCACAA TAGCAGCGGA GAAGGTGTAC AACACCCGCC ATCAGGAAGT         950
GCTTCGGGAG ATCCAGGATG CAGTGGCCAG GGCGGGGCAG GTGGTGCGGG        1000
AAGCCGTTGG AGGGCTGCAG ACCGTTCGCA GTTTTGGGGC CGAGGAGCAT        1050
GAAGTCTGTC GCTATAAAGA GGCCCTTGAA CAATGTCGGC AGCTGTATTG        1100
GCGGAGAGAC CTGGAACGCG CCTTGTACCT GCTCGTAAGG AGGGTGCTGC        1150
ACTTGGGGGT GCAGATGCTG ATGCTGAGCT GTGGGCTGCA GCAGATGCAG        1200
GATGGGGAGC TCACCCAGGG CAGCCTGCTT TCCTTTATGA TCTACCAGGA        1250
GAGCGTGGGG AGCTATGTGC AGACCCTGGT ATACATATAT GGGGATATGC        1300
TCAGCAACGT GGGAGCTGCA GAGAAGGTTT TCTCCTACAT GGACCGACAG        1350
CCAAATCTGC CTTCACCTGG CACGCTTGCC CCCACCACTC TGCAGGGGGT        1400
TGTGAAATTC CAAGACGTCT CCTTTGCATA TCCCAATCGC CCTGACAGGC        1450
CTGTGCTCAA GGGGCTGACG TTTACCCTAC GTCCTGGTGA GGTGACGGCG        1500
CTGGTGGGAC CCAATGGGTC TGGGAAGAGC ACAGTGGCTG CCCTGCTGCA        1550
```

| | |
|---|---|
| GAATCTGTAC CAGCCCACAG GGGGACAGGT GCTGCTGGAT GAAAAGCCCA | 1600 |
| TCTCACAGTA TGAACACTGC TACCTGCACA GCCAGGTGGT TTCAGTTGGG | 1650 |
| CAGGAGCCTG TGCTGTTCTC CGGTTCTGTG AGGAACAACA TTGCTTATGG | 1700 |
| GCTGCAGAGC TGCGAAGATG ATAAGGTGAT GGCGGCTGCC CAGGCTGCCC | 1750 |
| ACGCAGATGA CTTCATCCAG GAAATGGAGC ATGGAATATA CACAGATGTA | 1800 |
| GGGGAGAAGG GAAGCCAGCT GGCTGCGGGA CAGAAACAAC GTCTGGCCAT | 1850 |
| TGCCCGGGCC CTTGTACGAG ACCCGCGGGT CCTCATCCTG GATGAGGCTA | 1900 |
| CTAGTGCCCT AGATGTGCAG TGCGAGCAGG CCCTGCAGGA CTGGAATTCC | 1950 |
| CGTGGGGATC GCACAGTGCT GGTGATTGCT CACAGGCTGC AGACAGTTCA | 2000 |
| GCGCGCCCAC CAGATCCTGG TGCTCCAGGA GGGCAAGCTG CAGAAGCTTG | 2050 |
| CCCAGCTCTA G | 2061 |

(2) INFORMATION FOR SEQ ID NO: 18:

(i) SEQUENCE CHARACTERISTICS:
        (A) LENGTH: 2244 bases
        (B) TYPE: nucleic acid
        (C) STRANDEDNESS: single
        (D) TOPOLOGY: linear (ii) MOLECULE TYPE: other nucleic acid
        (A) DESCRIPTION: synthetic DNA fragment (xi) SEQUENCE DESCRIPTION: SEQ ID NO: 18:

| | |
|---|---|
| ATGGCTAGCT CTAGGTGTCC CGCTCCCCGC GGGTGCCGCT GCCTCCCCGG | 50 |
| AGCTTCTCTC GCATGGCTGG GGACAGTACT GCTACTTCTC GCCGACTGGG | 100 |
| TGCTGCTCCG GACCGCGCTG CCCCGCATAT TCTCCCTGCT GGTGCCCACC | 150 |
| GCGCTGCCAC TGCTCCGGGT CTGGGCGGTG GGCCTGAGCC GCTGGGCCGT | 200 |
| GCTCTGGCTG GGGGCCTGCG GGTCCTCAG GCAACGGTT GGCTCCAAGA | 250 |
| GCGAAAACGC AGGTGCCCAG GGCTGGCTGG CTGCTTTGAA GCCATTAGCT | 300 |
| GCGGCACTGG GCTTGGCCCT GCCGGGACTT GCCTTGTTCC GAGAGCTGAT | 350 |
| CTCATGGGGA GCCCCCGGGT CCGCGGATAG CACCAGGCTA CTGCACTGGG | 400 |
| GAAGTCACCC TACCGCCTTC GTTGTCAGTT ATGCAGCGGC ACTGCCCGCA | 450 |
| GCAGCCCTGT GGCACAAACT CGGGAGCCTC TGGGTGCCCG GCGGTCAGGG | 500 |
| CGGCTCTGGA AACCCTGTGC GTCGGCTTCT AGGCTGCCTG GGCTCGGAGA | 550 |
| CGCGCCGCCT CTCGCTGTTC CTGGTCCTGG TGGTCCTCTC CTCTCTTGGG | 600 |
| GAGATGGCCA TTCCATTCTT TACGGGCCGC CTCACTGACT GGATTCTACA | 650 |
| AGATGGCTCA GCCGATACCT TCACTCGAAA CTTAACTCTC ATGTCCATTC | 700 |
| TCACCATAGC CAGTGCAGTG CTGGAGTTCG TGGGTGACGG GATCTATAAC | 750 |
| AACACCATGG GCCACGTGCA CAGCCACTTG CAGGAGAGG TGTTTGGGGC | 800 |
| TGTCCTGCGC CAGGAGACGG AGTTTTTCCA ACAGAACCAG ACAGGTAACA | 850 |
| TCATGTCTCG GGTAACAGAG GACACGTCCA CCCTGAGTGA TTCTCTGAGT | 900 |
| GAGAATCTGA GCTTATTTCT GTGGTACCTG GTGCGAGGCC TATGTCTCTT | 950 |
| GGGGATCATG CTCTGGGGAT CAGTGTCCCT CACCATGGTC ACCCTGATCA | 1000 |
| CCCTGCCTCT GCTTTTCCTT CTGCCCAAGA AGGTGGGAAA ATGGTACCAG | 1050 |
| TTGCTGGAAG TGCAGGTGCG GGAATCTCTG GCAAAGTCCA GCCAGGTGGC | 1100 |

```
CATTGAGGCT CTGTCGGCCA TGCCTACAGT TCGAAGCTTT GCCAACGAGG         1150

AGGGCGAAGC CCAGAAGTTT AGGGAAAAGC TGCAAGAAAT AAAGACACTC         1200

AACCAGAAGG AGGCTGTGGC CTATGCAGTC AACTCCTGGA CCACTAGTAT         1250

TTCAGGTATG CTGCTGAAAG TGGGAATCCT CTACATTGGT GGGCAGCTGG         1300

TGACCAGTGG GGCTGTAAGC AGTGGGAACC TTGTCACATT TGTTCTCTAC         1350

CAGATGCAGT TCACCCAGGC TGTGGAGGTA CTGCTCTCCA TCTACCCCAG         1400

AGTACAGAAG GCTGTGGGCT CCTCAGAGAA AATATTTGAG TACCTGGACC         1450

GCACCCCTCG CTGCCCACCC AGTGGTCTGT TGACTCCCTT ACACTTGGAG         1500

GGCCTTGTCC AGTTCCAAGA TGTCTCCTTT GCCTACCCAA ACCGCCCAGA         1550

TGTCTTAGTG CTACAGGGGC TGACATTCAC CCTACGCCCT GGCGAGGTGA         1600

CGGCGCTGGT GGGACCCAAT GGGTCTGGGA AGAGCACAGT GGCTGCCCTG         1650

CTGCAGAATC TGTACCAGCC CACCGGGGGA CAGCTGCTGT TGGATGGGAA         1700

GCCCCTTCCC CAATATGAGC ACCGCTACCT GCACAGGCAG GTGGCTGCAG         1750

TGGGACAAGA GCCACAGGTA TTTGAAGAA GTCTTCAAGA AAATATTGCC          1800

TATGGCCTGA CCCAGAAGCC AACTATGGAG GAAATCACAC CTGCTGCAGT         1850

AAAGTCTGGG GCCCATAGTT TCATCTCTGG ACTCCCTCAG GGCTATGACA         1900

CAGAGGTAGA CGAGGCTGGG AGCCAGCTGT CAGGGGGTCA GCGACAGGCA         1950

GTGGCGTTGG CCCGAGCATT GATCCGGAAA CCGTGTGTAC TTATCCTGGA         2000

TGATGCCACC AGTGCCCTGG ATGCAAACAG CCAGTTACAG GTGGAGCAGC         2050

TCCTGTACGA AAGCCCTGAG CGGTACTCCC GCTCAGTGCT TCTCATCACC         2100

CAGCACCTCA GCCTGGTGGA GCAGGCTGAC ACATCCTCT TTCTGGAAGG         2150

AGGCGCTATC CGGGAGGGGG GAACCCACCA GCAGCTCATG GAGAAAAAGG         2200

GGTGCTACTG GGCCATGGTG CAGGCTCCTG CAGATGCTCC AGAA             2244
```

(2) INFORMATION FOR SEQ ID NO: 19:

(i) SEQUENCE CHARACTERISTICS:
        (A) LENGTH: 748 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 19:

```
Met Ala Ser Ser Arg Cys Pro Ala Pro Arg Gly Cys Arg Cys Leu Pro
              5                  10                  15

Gly Ala Ser Leu Ala Trp Leu Gly Thr Val Leu Leu Leu Ala Asp
         20                  25                  30

Trp Val Leu Leu Arg Thr Ala Leu Pro Arg Ile Phe Ser Leu Val
     35                  40                  45

Pro Thr Ala Leu Pro Leu Leu Arg Val Trp Ala Val Gly Leu Ser Arg
      50                  55                  60

Trp Ala Val Leu Trp Leu Gly Ala Cys Gly Val Leu Arg Ala Thr Val
 65                  70                  75                  80

Gly Ser Lys Ser Glu Asn Ala Gly Ala Gln Gly Trp Leu Ala Ala Leu
              85                  90                  95

Lys Pro Leu Ala Ala Ala Leu Gly Leu Ala Leu Pro Gly Leu Ala Leu
```

-continued

```
                    100                 105                 110
        Phe Arg Glu Leu Ile Ser Trp Gly Ala Pro Gly Ser Ala Asp Ser Thr
                115                 120                 125

Arg Leu Leu His Trp Gly Ser His Pro Thr Ala Phe Val Val Ser Tyr
            130                 135                 140

Ala Ala Ala Leu Pro Ala Ala Leu Trp His Lys Leu Gly Ser Leu
        145                 150                 155                 160

Trp Val Pro Gly Gly Gln Gly Gly Ser Gly Asn Pro Val Arg Arg Leu
                        165                 170                 175

Leu Gly Cys Leu Gly Ser Glu Thr Arg Arg Leu Ser Leu Phe Leu Val
                    180                 185                 190

Leu Val Val Leu Ser Ser Leu Gly Glu Met Ala Ile Pro Phe Phe Thr
                    195                 200                 205

Gly Arg Leu Thr Asp Trp Ile Leu Gln Asp Gly Ser Ala Asp Thr Phe
                210                 215                 220

Thr Arg Asn Leu Thr Leu Met Ser Ile Leu Thr Ile Ala Ser Ala Val
        225                 230                 235                 240

Leu Glu Phe Val Gly Asp Gly Ile Tyr Asn Asn Thr Met Gly His Val
                        245                 250                 255

His Ser His Leu Gln Gly Glu Val Phe Gly Ala Val Leu Arg Gln Glu
                    260                 265                 270

Thr Glu Phe Phe Gln Gln Asn Gln Thr Gly Asn Ile Met Ser Arg Val
                    275                 280                 285

Thr Glu Asp Thr Ser Thr Leu Ser Asp Ser Leu Ser Glu Asn Leu Ser
                290                 295                 300

Leu Phe Leu Trp Tyr Leu Val Arg Gly Leu Cys Leu Leu Gly Ile Met
        305                 310                 315                 320

Leu Trp Gly Ser Val Ser Leu Thr Met Val Thr Leu Ile Thr Leu Pro
                        325                 330                 335

Leu Leu Phe Leu Leu Pro Lys Lys Val Gly Lys Trp Tyr Gln Leu Leu
                    340                 345                 350

Glu Val Gln Val Arg Glu Ser Leu Ala Lys Ser Ser Gln Val Ala Ile
                    355                 360                 365

Glu Ala Leu Ser Ala Met Pro Thr Val Arg Ser Phe Ala Asn Glu Glu
                370                 375                 380

Gly Glu Ala Gln Lys Phe Arg Glu Lys Leu Gln Glu Ile Lys Thr Leu
        385                 390                 395                 400

Asn Gln Lys Glu Ala Val Ala Tyr Ala Val Asn Ser Trp Thr Thr Ser
                        405                 410                 415

Ile Ser Gly Met Leu Leu Lys Val Gly Ile Leu Tyr Ile Gly Gly Gln
                    420                 425                 430

Leu Val Thr Ser Gly Ala Val Ser Ser Gly Asn Leu Val Thr Phe Val
                    435                 440                 445

Leu Tyr Gln Met Gln Phe Thr Gln Ala Val Glu Val Leu Leu Ser Ile
                450                 455                 460

Tyr Pro Arg Val Gln Lys Ala Val Gly Ser Ser Glu Lys Ile Phe Glu
        465                 470                 475                 480

Tyr Leu Asp Arg Thr Pro Arg Cys Pro Pro Ser Gly Leu Leu Thr Pro
                        485                 490                 495

Leu His Leu Glu Gly Leu Val Gln Phe Gln Asp Val Ser Phe Ala Tyr
                    500                 505                 510

Pro Asn Arg Pro Asp Val Leu Val Leu Gln Gly Leu Thr Phe Thr Leu
                    515                 520                 525
```

```
Arg Pro Gly Glu Val Thr Ala Leu Val Gly Pro Asn Gly Ser Gly Lys
        530                 535                 540

Ser Thr Val Ala Ala Leu Leu Gln Asn Leu Tyr Gln Pro Thr Gly Gly
545                 550                 555                 560

Gln Leu Leu Asp Gly Lys Pro Leu Pro Gln Tyr Glu His Arg Tyr
            565                 570                 575

Leu His Arg Gln Val Ala Ala Val Gly Gln Glu Pro Gln Val Phe Gly
                580                 585                 590

Arg Ser Leu Gln Glu Asn Ile Ala Tyr Gly Leu Thr Gln Lys Pro Thr
            595                 600                 605

Met Glu Glu Ile Thr Ala Ala Val Lys Ser Gly Ala His Ser Phe
        610                 615                 620

Ile Ser Gly Leu Pro Gln Gly Tyr Asp Thr Glu Val Asp Glu Ala Gly
625                 630                 635                 640

Ser Gln Leu Ser Gly Gly Gln Arg Gln Ala Val Ala Leu Ala Arg Ala
                645                 650                 655

Leu Ile Arg Lys Pro Cys Val Leu Ile Leu Asp Asp Ala Thr Ser Ala
            660                 665                 670

Leu Asp Ala Asn Ser Gln Leu Gln Val Glu Gln Leu Leu Tyr Glu Ser
            675                 680                 685

Pro Glu Arg Tyr Ser Arg Ser Val Leu Leu Ile Thr Gln His Leu Ser
690                 695                 700

Leu Val Glu Gln Ala Asp His Ile Leu Phe Leu Glu Gly Gly Ala Ile
705                 710                 715                 720

Arg Glu Gly Gly Thr His Gln Gln Leu Met Glu Lys Lys Gly Cys Tyr
            725                 730                 735

Trp Ala Met Val Gln Ala Pro Ala Asp Ala Pro Glu
            740                 745
```

(2) INFORMATION FOR SEQ ID NO: 20:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: other nucleic acid
        (A) DESCRIPTION: synthetic DNA fragment (xi) SEQUENCE DESCRIPTION: SEQ ID NO: 20:

TAGTTTCATC TCTGGACTCC CTCA                                      24

(2) INFORMATION FOR SEQ ID NO: 21:

(i) SEQUENCE CHARACTERISTICS:
        (A) LENGTH: 22 bases
        (B) TYPE: nucleic acid
        (C) STRANDEDNESS: single
        (D) TOPOLOGY: linear (ii) MOLECULE TYPE: other nucleic acid
        (A) DESCRIPTION: synthetic DNA fragment (xi) SEQUENCE DESCRIPTION: SEQ ID NO: 21:

AGGTGTCTTT GCCTCGTCTT CT                                        22

(2) INFORMATION FOR SEQ ID NO: 22:

(i) SEQUENCE CHARACTERISTICS:

```
        (A) LENGTH: 24 bases
        (B) TYPE: nucleic acid
        (C) STRANDEDNESS: single
        (D) TOPOLOGY: linear (ii) MOLECULE TYPE: other nucleic acid
        (A) DESCRIPTION: synthetic DNA fragment (xi) SEQUENCE DESCRIPTION: SEQ ID NO: 22:

GCTACTAGTG CCTAGATGTG CAGT                                          24

(2) INFORMATION FOR SEQ ID NO: 23:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: other nucleic acid
        (A) DESCRIPTION: synthetic DNA fragment (xi) SEQUENCE DESCRIPTION: SEQ ID NO: 23:

CTTCTGCAGC TTGCCCTCCT GGAG                                          24
```

TRANSPORT ASSOCIATED PROTEIN SPLICE VARIANTS

FIELD OF THE INVENTION

The present invention relates to the discovery of nonallelic TAP polymorphs and to a new model of immune diversity based by this discovery. More specifically, the invention relates to TAP splice variants, which lead to the formation of a previously unknown class of MHC class I antigen complexes being presented to the immune system on MHC class I-presenting cells. A new layer of diversity is thus discovered for the immune system, in addition to the allelic variation in MHC class I molecules and the genetic rearrangements leading to diversity in the T cell receptor repertoire.

BACKGROUND OF THE INVENTION

Class II and class I proteins encoded by genes of the Major Histocompatability Complex (MHC) on chromosome 6 in humans play an essential role in regulating the immune system. MHC class II molecules, which are expressed in antigen-presenting cells such as macrophages, B cells, monocytes and some epithelial cells, form complexes with antigen peptides ("MHC class II antigen complexes") that are displayed on the surface of antigen-presenting cells for recognition by CD4+T lymphocytes (helper T cells). Helper T cell recognition results in release of lymphokines and T-dependent activation of B cells, which, in turn, lead to activation of macrophages and release of antibodies from B cells, leading to the killing or elimination of invading microorganisms. MHC class I molecules, which are expressed in virtually all nucleated cells, form complexes with antigen peptides ("MHC class I antigen complexes") that are displayed on the cell surface for recognition by CD8+cytotoxic T lymphocytes (CTLs). Presentation of an endogenous or "self" peptide by the MHC class I antigen complex is protective, the CTLs that would otherwise recognize the surface complex and attack the presenting cell (i.e., autoreactive CTLs) having been eliminated (deleted) from the immune system repertoire; and presentation of an exogenous (foreign or "non-self") peptide (or a mutated endogenous peptide) by the MHC class I antigen complex elicits CTL attack and cytolytic destruction of the infected or diseased cell.

The peptides that complex with MHC molecules are approximately eight to twenty-four amino acids in length. In the case of class II antigen complexes, the peptides are derived from partial proteolysis and processing of extracellular antigenic proteins incorporated by the cell through phagocytosis or pinocytosis or possibly surface processing. Thus, the immune recognition events mediated by MHC class II antigen complexes are a primary defense to invading microorganisms (e.g., bacteria, parasites) or foreign substances (e.g., haptens, transplant tissues) introduced to the cells of the immune system via the circulatory or lymph systems. In the case of class I antigen complexes, the antigen peptides are derived from intracellular processing of proteins. Thus, MHC class I antigen complexes either mark the cell as a normal endogenous cell, which elicits no immune response, or mark the cell as an infected cell (e.g., as in the case of a virus-infected cell exhibiting intracellularly processed viral peptide in the surface MHC class I complex) or a transformed cell (e.g., such as a malignant cell), which marks the cell for attack by CTLs.

Proper intracellular processing of antigen peptides for MHC class I complexing and presentation involves several steps. One of these steps is transport of the peptides from the cytosol into the endoplasmic reticulum (ER), where coupling of the antigen peptide with the MHC class I molecule takes place. The MHC class I antigen complex migrates to the cell surface for presentation and possible recognition by T cells. Unsuccessful transport of peptides into the ER, or other abnormalities leading to faulty class I antigen complex formation or presentation, can lead to a failure in recognizing autologous cells as "self". For example, defects in genes coding for transporter proteins have been discovered to be an underlying cause of several autoimmune diseases (Faustman et al., *Science*, 254:1756–1761 (1991); U.S. Pat. No. 5,538,854).

Transporter associated with Antigen Processing, or TAP, proteins transport peptide fragments of eight or more amino acids from the cytosol of a cell into the lumen of the ER, where the peptides are bound by MHC class I proteins to form an antigen complex, which ultimately is displayed on the surface of the cell (see, e.g., Powis et al., *Immunogenetics*, 37:373–380 (1990)). The TAP protein is a heterodimer of the products of the TAP1 and TAP2 genes, which are also located in the MHC region of the genome. Each subunit of the TAP1/TAP2 heterodimer forms an ATP-binding domain and a domain that criss-crosses the membrane six to eight times, and both subunits are required to form a peptide binding site and to translocate peptide into the ER (Androlewicz et al., *Proc. Natl. Acad. Sci. USA*, 91(26): 12716–12720 (1994); Hill et al., *Proc. Natl. Acad. Sci. USA*, 92: 341–343 (1995).)

The role of TAP in mediating the supply of antigen peptides transported into the ER and ultimately displayed by MHC class I molecules has caused close scrutiny of the range of peptides capable of translocation by TAP, to determine whether TAP is a further restrictive factor in immune diversity. (See, Hill et.al., ibid.; Howard., *Proc. Natl. Acad. Sci. USA*, 90: 3777–3779 (1993).) Whereas gene rearrangement during ontogeny of T cells generates an enormous variety of T cell receptor specificities, making the recognition capability of the immune system very diverse, there has not been discovered any corresponding mechanism for diversifying the presentation capability of an individual's immune system. Although small variations in MHC allotypes result in different repertoires of antigen peptides being complexed and presented by MHC molecules, lending diversity to antigen presentation across a species, an individual's MHC haplotypes restrict the range of antigens that can be effectively displayed. The specificity of the TAP transport mechanism also shapes the repertoire of antigen complexes presented to the immune system, in that only peptides capable of translocation by TAP are made available for complexing in the ER with MHC class I. (See, Howard, ibid.)

The peptide specificity of TAP proteins has been studied in three species thus far: human, mouse and rat. In the rat, it was shown that different alleles of the TAP2 gene gave rise to functional polymorphism, i.e., the different alleles transported sets of peptides that differed in C-terminal residues. (Powis et al., *Immunity*, 4(2):159–165 (1996); Powis et al., *Nature*, 357:211–215 (1992).) In the human and mouse, however, investigation of several polymorphs of TAP1 and TAP2 did not reveal any alteration in the spectrum of peptides transported, and it has been generally concluded that although in mice and humans the TAP1 and TAP2 proteins are genetically polymorphic, they are functionally monomorphic, the sequence alterations of the allotypes causing no shift in the types of peptides translocated by TAP. (Schumacher et al., *Proc. Natl. Acad. Sci. USA*, 91(26)

:13004–13008 (1994); Obst et al., *Eur. J. Immunol.*, 25:2170–2176 (1995); Daniel et al., *J. Immunol.*, 159:2350–2357 (1997).

It has now been discovered that the human TAP1 and TAP2 genes produce several splice variants that differ structurally and functionally from the known TAP1 and TAP2 proteins, and a functional TAP2 splice variant gene product, designated TAP2iso, has been characterized and its full coding sequence isolated. The TAP heterodimer including the TAP2iso splice variant, surprisingly, preferentially translocates a different set of peptides than the TAP heterodimer including TAP2. These discoveries have led to a revision described herein of the model of peptide transport into the lumen of the ER for MHC class I complexing; and a new level of diversity in the presentation of antigen complexes, akin in some respects to the diversity of T cell receptors in the recognition of such complexes, has been exposed for the first time.

SUMMARY OF THE INVENTION

The present invention to provides novel TAP1 and TAP2 splice variants and novel functional TAP heterodimers (i.e., a TAP1 subunit complexed with a TAP2 subunit) including at least one splice variant of TAP1 or TAP2. The TAP splice variants alter peptide transport to the ER in comparison with the previously known TAP complex. "Altered peptide transport" includes preferential transport of a specific repertoire of peptides that differs (e.g., in length or amino acid content or structure) from that transported by the previously known TAP protein (TAP1/TAP2 heterodimer), and/or a change in the rate of peptide transport into the ER as compared to known TAP. TAP splice variants according to the invention preferably measurably affect the repertoire of peptides displayed as MHC class I antigen complexes on the surface of antigen presenting cells or affect the cell surface density of particular MHC class I antigen complexes.

A specific embodiment of the present invention is designated TAP2iso (SEQ ID NO: 2). TAP2iso differs from the previously known TAP2 protein by a deletion of a C-terminal sequence corresponding to exon II of the human gene encoding TAP2 and the insertion in-frame with exon 10 of newly discovered exon 12 (SEQ ID NO: 5). Isolated nucleic acids encoding TAP2iso are also disclosed (see, e.g., TAP2iso cDNA, SEQ ID NO: 4). Further embodiments of this invention relate to additional TAP1 and TAP2 splice variants that have been detected by RT-PCR studies. Specific splice variants thus far detected are designated TAP1iso, TAP1iso$^2$ and TAP2iso$^2$.

The TAP1 and TAP2 splice variants of the present invention are unique arrangements and/or combinations of TAP1 and TAP2 exons. The TAP 1 and 2 splice variants are functional in that each splice variant complexes with at least one corresponding TAP subunit to form a TAP1-type subunit/TAP2-type subunit complex (a TAP heterodimer), which preferably is capable of translocating peptides.

The present invention relates also to novel TAP1 and TAP2 exons, by which the splice variants differ from known TAP1 and TAP2 coding sequences, and to the peptides encoded by those exons, which are useful, e.g., as immunogens for production of antibodies that can selectively recognize the splice variant proteins from mixed populations of TAP gene products.

The discovery of a genetic link to the repertoire of antigen peptides that are transported intracellularly to form MHC class I antigen complexes raises the possibility that variation in the complement of TAP1 or TAP2 gene products in humans will be associated with autoimmune disease. Thus, a deletion or a mutation in a splice variant exon may result in a failure to present certain endogenous peptides, leading in turn to autoreactive CTL attack of self tissues. Alteration of the ratio of co-expressed TAP subunit variants may also be associated with disease. And defective production of a particular variant of the TAP genes may provide an opening in the immune presentation-and-recognition system allowing malignant cells or virally infected cells to escape detection and to survive where they would be attacked and eliminated in another (normal) individual. This invention provides methods for detection and treatment of such disorders associated with abnormalities in TAP splice variant expression.

This invention also provides new methods for designing vaccines to broaden the immune response of individuals that may be unresponsive to a standard vaccine due to inadequate processing of particular viral antigens, for instance due to their expression of MHC class I alleles that do not efficiently display antigen peptides from available vaccine preparations. To broaden an individual's immune response to a particular virus, cells from the individual, e.g., lymphocytes (preferably macrophages, B cells or dendritic cells) may be withdrawn and transfected with a gene encoding a TAP isoform that is not expressed or poorly expressed in that individual, recover transfectants that express the inserted TAP isoform DNA, then return the cells to the individual. The TAP isoform gene may be non-specific, provided simply to broaden the range of peptides processed by the cells, or specific for providing translocation of particular viral antigen peptides. The transfected cells, expressing an additional TAP isoform will supplement the repertoire of antigen peptides processed and displayed to the immune system as MHC class I antigen complexes, leading to recognition by CD8-positive (CD8+) T cells and the development of T cell memory for those antigen complexes. Thereafter, the vaccinated individual will display a secondary antigen response to challenge from the virus. Similar methods will be useful for improving immune response against infectious diseases or tumor cells that escape an individual's normal antigen processing capability.

BRIEF DESCRIPTION OF THE DRAWINGS

FIGS. 9A and 9B show the comparative sequences of the PCR products indicating the presence of splice variants TAP1iso and TAP1iso$^2$ (FIG. 9A) and a schematic diagram of the genomic DNA including TAP1 exons 9–11, with diagrams of the TAP1iso and TAP1iso2 messages, both including exons 9 and 10 but two different segments of intron 10 (FIG. 9B).

DEFINITIONS

Figure 1:
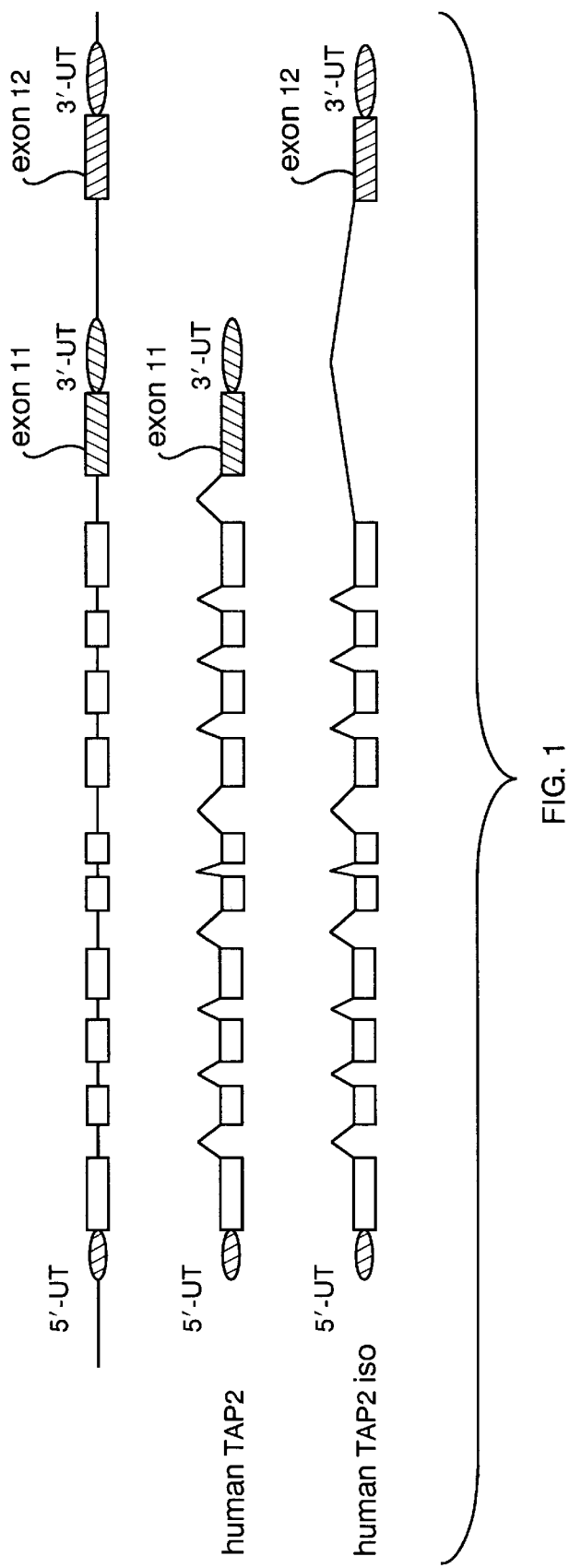
FIG. 1 depicts the organization of genomic human TAP2 genes and the structures of TAP2 and TAP2iso cDNAs. The open boxes represent exons 1 to 10, which, sharing the same 5' untranslated region (5'-UT), are present in both TAP2 and TAP2iso cDNAs. The alternatively spliced exons 11 and 12, together with their corresponding 3' untranslated regions (3'-UT), are hatched.

The following illustrative explanations are provided to facilitate understanding of certain terms and phrases frequently used and of particular significance herein.

The term "exon polypeptide", as used herein, refers to the peptide corresponding to the portion of a protein encoded by the DNA of a particular exon. Thus, the exon 12 polypeptide of the present invention, shown at SEQ ID NO: 1, is the polypeptide comprising the amino acids encoded by exon 12 of the TAP2iso coding sequence.

The term "splice variant", as used herein, refers to a gene product that is homologous to a known gene product and is generated by alternative RNA splicing during transcription. The splice variant will be partially identical in sequence to the known homologous gene product, corresponding to the extent of identity of exon use, comparing the mRNA transcripts (or cDNA), between the known product and the splice variant. Thus, the TAP2 splice variant described herein that is designated TAP2iso (SEQ ID NO: 2), is homologous to the previously known TAP2 protein (SEQ ID NO: 15), and the two gene products have common N-terminal amino acid sequences corresponding to the amino acids encoded by exons 1–10 of the TAP2 gene, and the amino acid sequences differ C-terminally to the exon 10 polypeptide, with TAP2 terminating with the exon 11 polypeptide (SEQ ID NO: 16) but TAP2iso terminating instead with the exon 12 polypeptide (SEQ ID NO: 1). By virtue of the partial identity and partial divergence of their amino acid sequences, the splice variant and the known homologues will have some functionality in common but will differ in other functions. For example, as shown herein, TAP2 and TAP2iso both (in a TAP complex with a TAP1 subunit) perform the function of translocating peptides into the lumen of the ER for MHC class I antigen complex assembly, but TAP2iso transports a repertoire of peptides that differs from that of TAP2, or transports the same peptides at a rate or with an efficiency that differs from TAP2.

The splice variants described herein form heterodimers with corresponding TAP subunits, and the functional TAP proteins formed by association of a splice variant with a known TAP subunit or by association of two splice variants are also new. TAP heterodimers including at least one subunit that is a splice variant will be referred to herein as "TAPiso" proteins, which will be understood to be comprised of one TAP1-type subunit and one TAP2-type subunit, where one or both of the subunits are splice variants of the known TAP1 and TAP2 subunits (e.g., TAP1iso/ TAP2, TAP1/TAP2iso, TAP1/TAP2iso$^2$ and TAP1iso/ TAP2iso heterodimers, and the like, are specific examples of "TAPiso proteins").

The term "homologous", as used herein, refers to the degree of sequence similarity between two polymers (i.e., polypeptide molecules or nucleic acid molecules). When the same nucleotide or amino acid residue occupies a sequence position in the two polymers under comparison, then the polymers are homologous at that position. The percent homology between two polymers is the mathematical relationship of the number of homologous positions shared by the two polymers divided by the total number of positions compared, the product multiplied by 100. For example, if the amino acid residues at 60 of 100 amino acid positions in two polypeptide sequences match or are homologous then the two sequences are 60% homologous. The homology percentage figures referred to herein reflect the maximal homology possible between the two polymers, i.e., the percent homology when the two polymers are so aligned as to have the greatest number of matched (homologous) positions.

The present invention further relates to isolated nucleic acids (or "polynucleotides") that hybridize to the TAP splice variant nucleic acid sequences described herein if there is sufficient homology between the TAP coding sequence and the complement of the homologous coding sequence to hybridize to each other under conditions equivalent to, e.g., about 20° to 27° C. below $T_m$ and 1M NaCl. The present invention particularly contemplates nucleic acid sequences that hybridize under stringent conditions to the TAP splice variant coding sequences described herein and complementary sequences thereof. For the purposes of this invention, the term "stringent conditions" means hybridization will occur only if there is at least 95% and preferably at least 97% identity between the nucleic acid sequences. Thus, the present invention particularly contemplates polynucleotides encoding TAP splice variants having the particular nucleic acid sequences described herein, or polynucleotides that are at least 95% identical to such sequences, and polynucleotides having sequences that are complementary to the aforementioned polynucleotides. The polynucleotides of the present invention that hybridize to the complement of TAP splice variant coding sequences described herein preferably encode polypeptides that retain substantially the same biological function or activity as the mature TAP2iso polypeptide encoded by the cDNA of SEQ ID NO: 4.

The term "isolated" means that the material is removed from its original or native environment (e.g., the natural environment if it is naturally occurring). For example, a naturally-occurring polynucleotide or polypeptide present in a living animal is not isolated, but the same polynucleotide or polypeptide, separated by human intervention from some or all of the coexisting materials in the natural system, is isolated. Such polynucleotides could be part of a vector and/or such polynucleotides or polypeptides could be part of a composition, and still be isolated in that such vector or composition is not part of the environment in which it is found in Nature. Similarly, as used herein, the term "substantially purified" is used in reference to a substance, which has been separated or otherwise removed, through human intervention, from the immediate chemical environment in which it occurs in Nature. Substantially purified polypeptides or nucleic acids may be obtained or produced by any of a number of techniques and procedures generally known in the field.

The present invention incorporates by reference methods and techniques well known in the field of molecular and cellular biology. These techniques include, but are not limited to techniques described in the following publications:

Old, R. W. & S. B. Primrose, *Principles of Gene Manipulation: An Introduction To Genetic Engineering* (3d Ed. 1985) Blackwell Scientific Publications, Boston. Studies in Microbiology; V.2:409 pp. (ISBN 0-632-01318-4).

Miller, J. H. & M. P. Calos eds., *Gene Transfer Vectors For Mammalian Cells* (1987) Cold Spring Harbor Laboratory Press, NY. 169 pp. (ISBN 0-87969-198-0).

Mayer, R. J. & J. H. Walker eds., *Immunochemical Methods In Cell and Molecular Biology* (1987) Academic Press, London. 325 pp. (ISBN 0-12480-855-7).

Sambrook, J. et al. eds., *Molecular Cloning: A Laboratory Manual* (2d Ed. 1989) Cold Spring Harbor Laboratory Press, NY. Vols. 1–3. (ISBN 0-87969-309-6).

Winnacker, E. L. From Genes To Clones: Introduction To Gene Technology (1987) VCH Publishers, NY (translated by Horst lbelgaufts). 634 pp. (ISBN 0-89573-614-4).

DESCRIPTION OF THE PREFERRED EMBODIMENTS

The present invention relates to the discovery of previously unknown isoforms homologous to the known TAP protein subunits (TAP1 and TAP2, see SEQ ID NOS: 18 and 17 (coding sequences) and SEQ ID NOS: 19 and 15 (amino acid sequences)). The newly discovered isoforms are the result of alternate RNA splicing and are co-expressed with the known TAP1 and TAP2 gene products, providing a plurality of TAP heterodimers functioning to translocate antigen peptides from the cytoplasm into the endoplasmic reticulum for complexing with MHC class I molecules and formation of MHC class I antigen complexes. The splice variant isoforms have been found to form TAP heterodimers that transport a different repertoire of peptides or that transport similar peptides at different rates (i.e., with greater or lesser efficiency) than the known TAP1/TAP2 heterodimers; and the discovery of these alternate TAP transporter proteins exposes a genetic mechanism of diversification in the process of class I antigen presentation. Co-expression of multiple TAP1 and TAP2 splice variants provides a diverse family of transporters capable of translocating a wider range of antigen peptides from the cytosol to the ER and increasing the repertoire of MHC class I antigen complexes presented to the immune system. It is through such diversification mechanisms that it is now demonstrated that the antigen processing and presentation mechanisms of the immune system are able to drive and select T cell response diversity on the recognition side of the immune system, which is based on the enormous diversity of the T cell receptor (TCR).

Specific embodiments of the invention include novel splice variants of TAP1 and TAP2 and nucleic acids that encode them. Specific splice variants described herein are designated TAP1iso, TAP1iso$^2$, TAP2iso and TAP2iso$^2$. The invention further encompasses novel TAP heterodimers ("TAPiso" heterodimers) incorporating the splice variants, exon polypeptides corresponding to previously unknown segments of the splice variants (i.e., corresponding to the exons by which the splice variants differ from known TAP1 or TAP2), vectors for cloning and expression of the splice variants or novel exon polypeptides, and recombinant host cells capable of expressing the splice variants, exon polypeptides or TAPiso heterodimers. The nucleotide sequence of TAP2iso and the deduced amino acid residue sequence of TAP2iso are shown in the Sequence Listing (SEQ ID NO: 4 and SEQ ID NO: 2, respectively).

The discoveries of the present invention also raise the possibility that a deletion or defect in expression of a particular TAP1 or 2 isoform, or that an abnormal expression level of one TAP1 or 2 isoform with respect to another, may cause the manifestation of autoimmune disease. Methods for diagnosis and methods of treatment of such diseases associated with defective TAP isoform expression are described herein.

An isolated nucleic acid (polynucleotide) that encodes the mature TAP2iso polypeptide having the deduced amino acid sequence of SEQ ID NO: 2 has been deposited under the Budapest Treaty with ATCC (American Type Culture Collection, 12301 Parklawn Drive, Rockville, Md. 20852 U.S.A.) under accession no. 209640 on Feb. 24, 1998.

The ATCC microorganism deposit referred to above will be maintained under the terms of the Budapest Treaty on the International Recognition of the Deposit of Microorganisms for purposes of Patent Procedure. The deposit is provided as a convenience to those of skill in the art and is not to be construed as an admission that such a deposit is required under 35 U.S.C. §112 or is necessary for a complete understanding of the invention. The sequence of the polynucleotides contained in the deposited material, as well as the amino acid sequence of the polypeptides encoded thereby, is incorporated herein by reference and is controlling in the event of any conflict with any description of sequences herein. A license may be required to make, use or sell the deposited material, and no such license is hereby granted.

Isolation of TAP Subunit Splice Variants

Nucleic acids coding on expression for TAP1 or TAP2 splice variants according to this invention may be isolated by screening a cDNA library, such as a human splenocyte cDNA library. cDNA libraries may be screened using an oligonucleotide probe complementary to an exon of TAP1 or TAP2 (or, also, a probe complementary to an intron portion suspected of being an exon in a splice variant). Construction of suitable cDNA libraries is well known in the art. Any portion of a TAP1 or TAP2 mRNA or cDNA may be used, however it is preferred that the probe be designed so as not to span exons and to include coding sequences that are thought to be used in all isoforms. Thus far, variation in the TAP1 and TAP2 coding sequences has been discovered at the 3' end of the sequences, and therefore it is preferred to screen using probes based on the first nine or ten exons of TAP1 and TAP2. Probes based on all or part of exon 10 of TAP1 or TAP2 are most preferred.

Additional TAP subunit splice variants may be isolated using reverse transcription polymerase chain reaction (RT-PCR) techniques: Now that the existence of TAP splice variants has been disclosed, additional coding sequences for splice variants can be discovered by analysis of PCR products from segments of total RNA and mRNA (see the examples, infra). Forward and reverse PCR primer pairs can be designed from genomic sequence information disclosed herein or obtained elsewhere. The RT-PCR experiments set forth herein were greatly assisted by genomic sequence information on human chromosome 6 (which includes the TAP genes) that was generously provided by Dr. John Trowsdale and colleagues at the Imperial Cancer Research Fund, London. Primer pairs can be selected to amplify any segment of the TAP loci or, in RT-PCR, any segment of cDNA derived from total RNA, however it is preferred to select primer pairs that are about 300–500 bp apart, so that disparate co-amplified products can be readily distinguished, e.g., by separation on an electrophoresis gel. It is preferred to employ overlapping primer sets for investigation of adjacent segments, and it is preferred to verify unexpected RT-PCR products by amplifying the same region using different primer sets.

The TAP splice variants described herein were first detected when attempts to isolate monoclonal antibodies recognizing either N-terminal or C-terminal epitopes of the known TAP subunits failed to yield C-terminal antibodies that would clear a lysate containing TAP subunits of all TAP products, whereas antibodies recognizing the N-terminus were capable of clearing solutions of all TAP products.

It was decided to examine TAP1 and TAP2 RNA samples using reverse transcription polymerase chain reaction (RT-PCR) analysis to see if plural messages were being generated. A series of forward and reverse primers were prepared for examining segments of the TAP1 and TAP2 coding sequences. Primers were selected to bracket relatively small segments of the genomic sequence (e.g., 300–500 bp apart), and overlapping primer sets were used (i.e., sets of primers suitable for PCR-amplifying overlapping segments of DNA).

TAP2iso cDNA was isolated from a human splenic cDNA library using an oligonucleotide probe (19 bp, SEQ ID NO: 3) complementary to exon 10 of the known TAP2 coding sequence. The TAP2iso coding sequence is set forth in the Sequence Listing as SEQ ID NO: 4; the deduced amino acid sequence for TAP2iso is shown at SEQ ID NO: 2. The TAP2iso polynucleotide (SEQ ID NO: 4) encodes a polypeptide of 653 amino acids. Amino acids 1–644 are identical to a previously characterized TAP2 (SWISS-PROT: Q03519; SEQ ID NO: 15), and the rest of the C-terminal nine amino acids are encoded by an alternatively spliced exon 12 (SEQ ID NO: 5). The novel peptide corresponding to the coding sequence of exon 12 (SEQ ID NO: 5) is referred to as the exon 12 peptide (SEQ ID NO: 1).

The polynucleotides of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequences for splice variant TAP isoforms according to the present invention will be partially identical and partially different (e.g., <50% homologous) to the known TAP coding sequences (i.e., TAP1 or TAP2, SEQ ID NOS: 18 and 17, respectively). The TAP2iso coding sequence may be identical to the coding sequences shown in the Sequence Listing section (e.g., SEQ ID NO: 4) or identical to that of the deposited clone or may be a different coding sequence, which different coding sequence, as a result of the redundancy or degeneracy of the genetic code, encodes the same polypeptide.

The present invention further relates to TAPiso transporter proteins, TAP1iso and TAP2iso splice variant proteins, and exon polypeptides. Such TAP1 and TAP2 splice variants will be partially identical and partially different (e.g., <50% homologous) to the known TAP1 and 2 subunits (i.e., SEQ ID NOS: 19 and 15, respectively); and TAPiso transporter proteins will be correspondingly partly identical and partly different from the known TAP transporter protein that consists of the heterodimer formed from TAP1 and TAP2. Exon polypeptides corresponding to previously unknown exons will have coding and amino acid sequences differing substantially from any known exon of TAP1 or TAP2. Specifically contemplated are TAP2iso proteins or exon polypeptides that have the deduced amino acid sequences of SEQ ID NOS: 1 and 2 or that have the amino acid sequence encoded by the deposited cDNA, as well as fragments thereof encoding polypeptides having the same biological function or activity as such polypeptides. The TAPiso polypeptides of the present invention may be recombinant polypeptides (i.e., non-naturally occurring polypeptides produced using recombinant DNA techniques), natural polypeptides or synthetic polypeptides, preferably recombinant polypeptides.

Homologues of the TAP1iso and TAP2iso polypeptides and exon polypeptides described herein may be formed by substitution, addition or deletion of one or more amino acids employing methods well known in the art and for particular purposes known in the art, such as addition of a polyhistidine "tail" in order to assist in purification or substitution of one up to several amino acids in order to obliterate an enzyme cleavage site. Preferably such homologues will retain functionality as subunits able to dimerize with counterpart TAP or TAPiso subunits in order to provide a functional TAP (TAPiso) protein capable of translocating peptides in a cell.

The polypeptides and polynucleotides of the present invention are preferably provided in an isolated form, and preferably are purified to homogeneity.

The present invention also provides vectors that include TAPiso polynucleotides of the present invention, host cells that are genetically engineered with vectors of the invention, polypeptides produced by culturing such genetically engineered host cells. Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the TAPiso genes. The culture conditions, such as temperature, pH and the like, are those suitable for use with the host cell selected for expression and will be apparent to the ordinarily skilled artisan.

The polynucleotides of the present invention may be employed for producing polypeptides by recombinant DNA techniques or, preferably, for transfecting cells to augment their capability to translocate cytosolic peptides to the ER for complexing with MHC class I molecules and eventual antigen display. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host. The appropriate DNA sequence may be inserted into the vector by a variety of procedures. In general, the DNA sequence is inserted into an appropriate restriction endonuclease site(s) by procedures known in the art. Such procedures and others are deemed to be within the skill of those skilled in the art.

The DNA sequence in the expression vector is operatively linked to an appropriate expression control sequence(s) (promoter) to direct mRNA synthesis. As representative examples of such promoters, there may be mentioned LTR or SV40 promoter, the *E. coli.* lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression. In addition, expression vectors preferably will contain one or more selectable marker genes to provide a phenotypic trait for selection of transformed host cells, such as dihydrofolate reductase or neomycin resistance for eukaryotic cell culture, or such as tetracycline or ampicillin resistance for bacterial cell cultures such as *E. coli.*

The vector containing the appropriate TAP DNA sequence as hereinabove described, as well as an appropriate promoter or control sequence, may be employed to transform an appropriate host to permit the host to express the protein.

As representative examples of appropriate host cells, there may be mentioned bacterial cells, such as *E. coli*, Streptomyces, *Salmonella typhimurium*; fungal cells, such as yeast; insect cells such as Drosophila and Sf9; animal cells such as CHO, COS or Bowes melanoma; plant cells, etc. However, where the object of transfection of the host cell is to form operative intracellular TAPiso proteins to augment or restore the capability of a cell to transport a particular antigen peptide or group of peptides, then mammalian cells, such as CHO or COS cells, or more particularly human cell lines, such as T cell or B cell lines, T1 or T2 cells (see infra), HeLa cells, U-937 cells, EBV-immortalized human B cell lines, PACA cells, and the like, are much preferred. The selection of an appropriate host is deemed to be within the skill of those skilled in the art from the teachings herein. Many suitable vectors and promoters useful in expression of proteins according to this invention are known to those of skill in the art, and many are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). Any other plasmid or vector may be used as long as it is replicable and viable in the selected host cell.

Introduction of the vectors into the host cell can be effected by any known method, including calcium phosphate transfection, DEAE-Dextran mediated transfection, or electroporation. (see Davis et al., *Basic Methods in Molecular Biology*, (1986)).

The constructs in host cells can be used in a conventional manner to produce the TAP gene product encoded by the recombinant sequence. Alternatively, the polypeptides of the invention can be synthetically produced by conventional peptide synthesizers. The TAP polypeptides and exon polypeptides of the present invention can be recovered and purified from recombinant cell cultures by suitable methods including ammonium sulfate or ethanol precipitation, acid extraction, anion or cation exchange chromatography, phosphocellulose chromatography, hydrophobic interaction chromatography, affinity chromatography, hydroxylapatite chromatography, lectin chromatography, and the like. High performance liquid chromatography (HPLC) can be employed for final purification steps. The novel polypeptides of the present invention may be a naturally purified products, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated.

Functional Activity of TAP Subunit Splice Variants

TAPiso proteins according to the present invention preferably exhibit the same general functionality as known TAP transporter proteins, namely, translocation within a cell of peptides from the cytosol into the ER. However, the discoveries detailed herein demonstrate that the specific functionality of different TAP proteins, formed from different pairings of TAP1 and TAP2 isotypes, can lead to different classes of peptides being translocated, or the same peptide being translocated preferentially or at a different rate in comparison to other peptides.

Several ways of measuring TAP protein functionality are discussed below:

A. Transport Efficiency

The rate at which different TAP isoforms transport cytosolic peptides into the ER (transport efficiency) is one way to distinguish between homologous isoforms and one basis for TAP-mediated diversity in the presentation of MHC class I antigen complexes. The transport efficiency of TAPiso proteins may be compared with that of previously characterized TAP proteins using experimental techniques such as those of the following examples.

The rate at which MHC class I antigen complexes exit the ER can be used as one measure of TAP protein transport efficiency. MHC class I does not leave the ER until and unless it complexes with an appropriate peptide. TAP transport of peptides is the sole source of cytosolic peptides in the ER. The level of a particular MHC class I antigen complex within the Golgi apparatus of a cell, therefore, is directly proportional to TAP transport of the antigen peptide into the ER.

A preferred method of measuring the rate at which MHC class I antigen complexes exit the ER is through the quantification of MHC class I proteins of the Golgi apparatus sensitive to endoglycosidase H (endo H). Glycosylation of MHC class I proteins in the Golgi apparatus results in an increase in their molecular mass and an increase in resistance of MHC class I-linked glycans to endo H. By [$^{35}$S] methionine pulse-labeling TAP- or TAPiso-expressing cell cultures and chasing with unlabeled methionine at various times, the rate of MHC class I maturation in the ER can be gauged by observing differences in endo H sensitivity, e.g., compared with a TAP-deficient cell line such as T2. (See, FIGS. 4A and 4B.)

B. Peptide Selectivity

Differential peptide binding specificity (peptide selectivity) is another way in which TAP isoforms may differ. All previously studied human allelic TAP polymorphs have shown no differences in peptide selectivity, however the nonallelic splice variants of the present invention have shown differences in peptide selectivity in comparison with previously studied TAP proteins.

The peptide binding domain of TAP proteins requires both a TAP1 and a TAP2 subunit. TAPiso transporter proteins including at least one TAPiso splice variant as disclosed herein, may result in the binding and translocation of a distinct class of cytosolic peptides, compared to those bound and translocated by a TAP1/TAP2 complex. This differential peptide selectivity has been demonstrated for TAP1/TAP2iso in comparison to TAP1/TAP2 (see examples, infra), thus the co-expression of TAP1 and TAP2 isoforms lead to diversification in peptides loaded into MHC class I molecules for antigen presentation at the cell surface.

The function of TAP proteins and the transport of different peptide repertoires can by tested by supplying known peptides, which may be labeled for ease of detection, to TAP and TAPiso transformants and comparing their abilities to transport peptide into the ER and the rate at which transport is effected. Test peptides will preferably be of an optimal length for transport, i.e., about 6–25 amino acids in length, most preferably 8–12 amino acids in length. In a preferred assay of translocation, the test peptides are labeled with radioactive iodine ($^{125}$I). Additionally, glycosylation of the peptides within the ER of the MHC class I antigen complex can be monitored as an indication that successful transport and maturation of a properly formed antigen complex is taking place. One preferred method of monitoring maturation is noting increased resistance to endoglycosidase H (endo H), the principle being that as N-linked glycosylation of the MHC class I molecule proceeds to completion, the glycan structures of the protein become less susceptible to endo H cleavage.

Competitive inhibition techniques can also be used to compare translocation specificities of different TAP proteins. In such assays, two or more test peptide moieties are provided for possible transport by TAP proteins. Preferential TAP transport of a test peptide is measured by the competitive inhibition of the peptides in relation to each other. For example, one test peptide is detectably labeled (e.g., $^{25}$I-labeled), and a second test peptide, labeled or unlabeled, is introduced into the cell, and the effect of the second peptide on the detectable translocation of the first test peptide is measured.

C. Restoration of Surface MHC Class I Antigen Complex Presentation

Functional TAPiso proteins of the present invention will bind and translocate peptides into the ER for MHC class I loading and eventual cell surface presentation. One preferred technique to measure the functionality of TAP1 and TAP2 isoforms, therefore, is to measure restoration of MHC class I antigen presentation in a TAP-deficient cell line, such as T2 cells (Attaya et al., Nature, 355:647 (1992)). A TAP-deficient cell can be transfected with TAP1 and TAP2 genes to express a functional TAP or TAPiso transporter protein, and the extent of restoration of surface MHC class I antigen presentation on the transfected cell can then be measured.

The TAPiso genes described herein, and the TAPiso expression products and related exon polypeptides, will have many uses in the field of immunology and immunotherapy. For example, the TAPiso genes may be used to prepare recombinant host cells expressing only a particular TAPiso transporter protein, which cell will be useful in defining the specificity and translocation efficiency of particular TAPiso proteins. The TAPiso genes also may be used to produce useful quantities of isolated TAP1iso or TAP2iso proteins, which may be used as immunogens for the production of monoclonal or polyclonal anti-TAP subunit antibodies or anti-exon polypeptide antibodies for use as diagnostic reagents or cell classification markers.

The TAPiso expression products or their fragments (including exon polypeptides), or cells expressing them, can be used as immunogens to produce antibodies recognizing such products or fragments. These antibodies can be, for example, polyclonal, monoclonal, chimeric, single-chain, Fab fragments, or the product of a Fab expression library. Various procedures are known in the art for the production of such antibodies. Antibodies generated against the polypeptide corresponding to a sequence of the present invention can be obtained by direct injection of the polypeptide into an animal or by administering the polypeptide to an animal, preferably a nonhuman animal. The antibody so obtained will then recognized or bind to the polypeptide itself. In this manner, even a sequence encoding only a fragment of a TAP1iso or TAP2iso polypeptide can be used to generate antibodies binding the whole native polypeptide. Such antibodies can then be used to isolate the polypeptide from tissue expressing that polypeptide or to detect expression of a particular TAP subunit or formation of a particular TAP or TAPiso transporter protein in particular cells or tissues. Moreover, a panel of anti-TAP1 or anti-TAP2 or anti-TAP antibodies, specific to a range of TAP subunits and/or TAP heterodimers, can be used to identify and differentiate tissues and disease states corresponding with differential expression of TAP subunits or differential formation of TAP transporters.

For preparation of monoclonal antibodies, any technique that provides antibodies produced by continuous cell line cultures can be used. Well known examples of such techniques include the hybridoma technique (Kohler and Milstein, *Nature*, 256:495–497 (1975)), the trioma technique, the human B-cell hybridoma technique (Kozbor et al., *Immunology Today*, 4:72 (1983)), and the EBV-hybridoma technique to produce human monoclonal antibodies (Cole et al., *Monoclonal Antibodies and Cancer Therapy*, Alan R. Liss, Inc., pp. 77–96 (1985)).

Techniques described for the production of single-chain antibodies in U.S. Pat. No. 4,946,778 can be adapted to produce single-chain antibodies recognizing immunogenic polypeptide products of this invention.

Such antibodies can be used in methods relating to the localization and activity of the TAP expression products described herein, e.g., for imaging these proteins, measuring levels thereof in appropriate physiological samples, and the like.

The TAPiso polynucleotides of the present invention also provide a means for screening candidate drugs to identify those capable of enhancing or inhibiting peptide transport. Such candidate drugs would be useful in upregulating or downregulating the immune response to particular antigens or for treating disorders associated with a particular ratio of TAP expression products produced by an individual. For example, where an immune disorder is associated with higher than normal expression of a particular TAP protein or a higher than normal expression in relation to another TAP protein, then modulation of one or the other expression products to correct the expression or balance the relative expression of TAP proteins can alleviate the manifestation of the disorder. For drug candidate screening, a mammalian cell or membrane preparation expressing one or more TAP proteins can be incubated with labeled peptides in the presence of the drug candidate. The ability of drug to change the rate of translocation of the peptides by the TAP protein(s) or to block the translocation can then be measured.

The TAPiso polynucleotides of the present invention may also be employed in accordance with the present invention for causing expression of TAPiso polypeptides in vivo, which is often referred to as "gene therapy". For example, cells from a patient may be transfected with a polynucleotide (DNA or RNA) encoding a TAP polypeptide ex vivo, using known transfection techniques. The resultant transfectants expressing the introduced polynucleotide can reverse a TAP deficiency in the host cell, or supplement low expression of a particular subunit by the host cell, or provide an additional TAP transporter protein in the cell, thus augmenting the repertoire of MHC class I antigen complexes that are displayed by the host cell. The transfectants then can be provided to a patient to be treated. Such gene therapy methods are well known in the art.

Similarly, cells may be engineered in vivo for expression of a TAP polypeptide in vivo by procedures known in the art. For instance, a cell producing a retroviral particle containing RNA encoding the TAP polypeptide of interest may be administered to a patient for infection and transformation of the patient's cells in vivo and expression of the particular TAP polypeptide in vivo. Alternatively, known microinection techniques can be employed to insert plasmid DNA into cells of a patient, thereby augmenting the class I antigen display of those cells and prompting a desired immune response. These and other methods for administering the polynucleotides or using a polypeptide of the present invention will be apparent to those skilled in the art from the foregoing description and the examples to follow.

In addition to gene therapy, the TAP splice variants disclosed herein may be used in improving vaccine designs or in overcoming weak immune responses in an individual to a pathogen. For example, there may be viruses that are able to avoid immune detection and attack in certain individuals because of inadequate transport of viral antigen peptides into the ER for complexing with MHC class I molecules and ultimate presentation on the cell surface. Such viruses expose a "hole" in the immune system, i.e., a gap in the antigen presentation repertoire that leads to an inability of the immune system to recognize and respond to the viral antigens, even though there are T cells bearing receptors expressed by the individual capable of binding the antigens if properly presented. Where such inadequate transport of viral antigen peptides is the result of low expression or no expression of particular TAP variants, the TAP1 and TAP2 genes disclosed herein can be used to broaden the immune responsiveness of an individual. A preferred method for broadening an individual's immune responsiveness is by ex vivo transfection of MHC class I expressing cells, preferably lymphocytes, most preferably B cells, macrophages or dendritic cells, with DNA encoding TAP isoforms that are not expressed or are expressed at low levels, followed by reintroduction of the transfected cells into the individual, where the expression of additional TAP isoforms leads to presentation of additional antigen peptides, which, in turn, drives selection and proliferation of responsive T cells. The DNA encoding the non-expressed or inadequately expressed TAP isoform used in transfection may be specific or non-specific for the antigens derived from a particular pathogen, that is, the range of antigen peptides and thus the repertoire of displayed antigen complexes will be broadened by transfecting DNA encoding any supplementary isoform of TAP, but alternatively, if it is determined what antigen peptides result from proteolysis of a particular virus and if it is determined that the function of a particular TAP isoform leads to the translocation of such antigen peptides, then the transfection using the appropriate TAP isoform-encoding DNA will tailor the broadened immune response to the particular virus by causing an increase in the MHC class I/viral antigen complexes being presented by transfected cells. The effect of this vaccination will also continue past the cell in vivo life of the transfectants, because transient presentation of the supplemental repertoire of viral antigens will establish a T cell memory, and the individual challenged subsequently by the same virus will be able to mount a classic secondary antigen response.

This approach can also be used to address infectious diseases, especially where an individual's susceptibility to a disease is due to inadequate expression of a particular TAP isoform. In this way an individual can also be vaccinated to fight malignancies that escape immune attack due to inadequate presentation of antigen peptides associated with the malignant tissues. This approach would be especially useful in cases where a family history revealed a predisposition for developing certain cancers, such as breast cancer. If individuals from that family also showed abnormal expression of any of the TAP isoforms, transfected cell therapy could be used to correct the TAP deficiency or to balance the levels of expression of TAP isoforms to reflect normal levels.

EXAMPLE 1

TAP2iso

Figure 2:
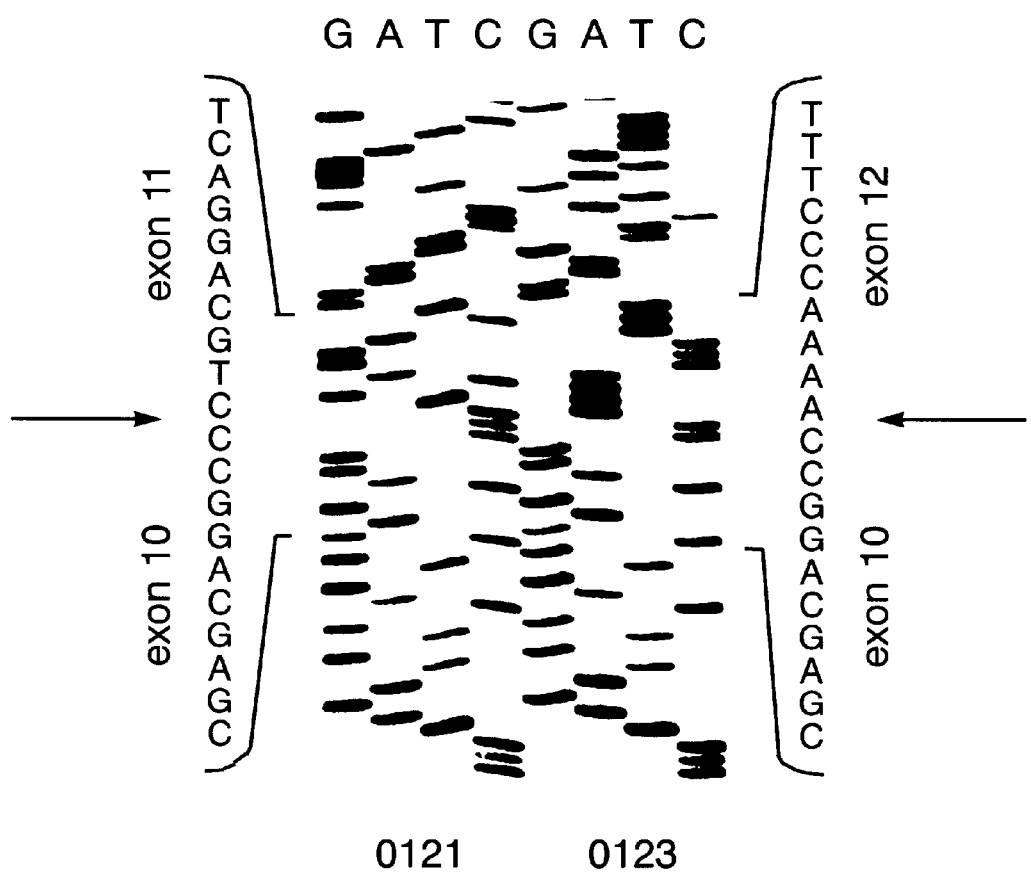
FIG. 2 illustrates the sequence analysis of the exon junctions of TAP2 (clone 0121) and TAP2iso (clone 01023) cDNAs isolated from the same human spleen cDNA library. Two full-length cDNA clones, 0121 and 0123, represent two different forms of human TAP2 cDNA. Clone 0121 corresponds to the previously described TAP2 isoform, in which exon 10 is spliced at transcription to exon 11. Clone 0123 represents the discovered TAP2iso cDNA, in which exon 10 is spliced to exon 12.
Figure 3:
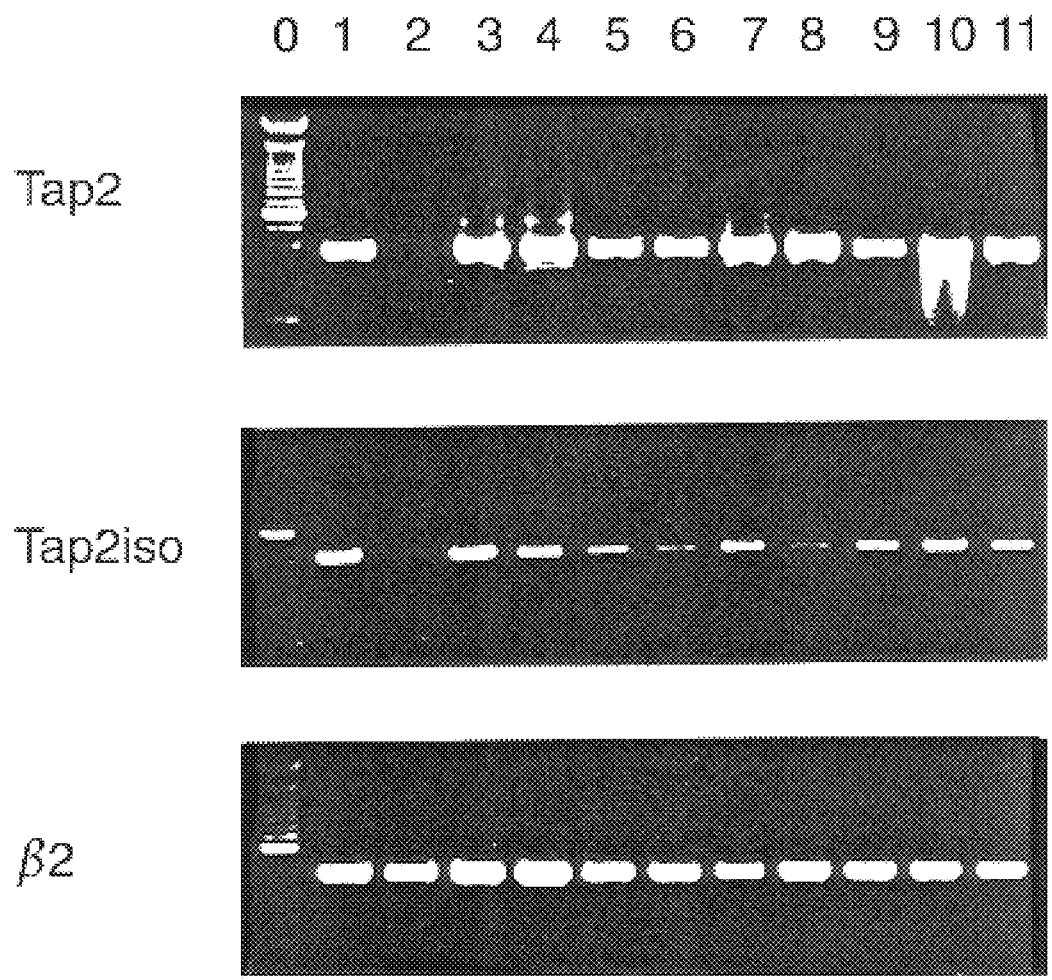
FIG. 3 illustrates electrophoresis results of RT-PCR products showing co-expression of TAP2 and TAP2iso mRNAs in various human cell lines, along with $\beta_2$-microglobulin ($\beta$2). Lanes: (0) DNA molecular size markers; (1) T1 cells (human lymphoblastoid B cell line); (2) T2 cells (human lymphoblastoid B cell line of T1 origin with a large homozygous deletion of the MHC class II gene region containing TAP1 and TAP2); (3 and 4) fresh human peripheral blood lymphocytes from two different donors; (5 and 6) Epstein-Barr virus-immortalized B cell lines from two different donors; (7) MOLT-4 acute lymphoblastic leukemia cells; (8) THP-1 monocytic cells; (9) U-937 histocytic lymphoma cells; (10) HeLa epithelioid carcinoma cells; (11) PACA pancreatic carcinoma cells.

Described below is the isolation and characterization of a novel TAP2 splice variant (i.e., TAP2iso) that, when complexed with TAP1, forms a novel TAP heterodimer distinct from the known TAP transporter protein. TAP2iso lacks TAP2 exon 11 and contains a newly-identified TAP2 exon 12, located 6533 base pairs (bp) downstream of TAP2 exon 11 (see FIG. 1). The 2496 bp full-length cDNA of TAP2iso (see SEQ ID NO: 4) predicts a protein of 653 amino acids (SEQ ID NO: 2), the last nine of which are encoded by exon 12 (FIGS. 2 and 3). The protein encoded by this cDNA shows the ability to dimerize with TAP1 and to form a peptide-transporting heterodimer, however that TAP1/TAP2iso transporter exhibits characteristics that differ from those of the previously identified TAP.

Isolation of TAP2iso

The existence of heterofunctional TAP1 and 2isoforms was detected during the course of work to isolate antibodies to the C-terminus of each of the known TAP subunits, TAP1 and TAP2. Whereas polyclonal antibodies recognizing epitopes of the N-terminal sequences of TAP1 and TAP2 had been isolated which would clear a cell lysate of all TAP expression products, polyclonal antibodies raised against the known C-terminal sequences were unable to remove all TAP proteins from a solution. One explanation of this phenomenon was that there were variant isoforms of the known TAP subunits differing at the C-terminal end to a sufficient degree that they could not be recognized by antibodies raised against only the known C-terminal sequences. Since a polyclonal antiserum would be expected to clear all of the known polymorphs of TAP1 and TAP2, it was decided to search for TAP1 and 2 splice variants exhibiting entirely heterologous C-terminal sequences compared to the known TAP1 and 2 proteins.

It was decided to examine a cDNA library with probes complementary to a sequence coding for an upstream segment of the TAP1 and TAP2 proteins, to see if variant transcripts could be detected. Probes were designed using sequence information of the entire locus including the known TAP genes, generously provided by Dr. John Trowsdale and colleagues at the Imperial Cancer Research Fund, London. When a specific 19-base pair (bp) oligonucleotide probe complementary to exon 10 of TAP2 was used to screen a human spleen cDNA library prepared from a single individual, two different full-length transcripts were detected and analyzed.

The human splenic cDNA library was screened with the use of a soluble hybridization system (Gene Trapper; Gibco-BRL). The specific oligonucleotide probe (5'-ATGTAGGGGAGAAGGGAAG-3', identified as SEQ ID NO: 3) targeted to exon 10 of TAP2 was synthesized and purified by electrophoresis on a 12% polyacrylamide gel [acrylamide: bisacrylamide, 19:1 (w/w)] containing 8 M urea with 1× Tris-borate-EDTA buffer. The probe (3 µg) was biotinylated with the use of terminal deoxynucleotidyl transferase and biotin-conjugated deoxycytidine triphosphate. The cDNA library was digested for 25 minutes at 25° C. with Gene II (Gibro-BRL), an enzyme that introduces random nicks into DNA, and then for 60 minutes at 37° C. with *Escherichia coli* exonuclease III to generate single-stranded plasmid DNA. Hybridization between single-stranded plasmid DNA and 20 ng of the biotinylated probe was performed in solution for 60 minutes at 37° C. The mixture was then incubated for an additional 20 minutes with streptavidin-coated magnetic beads, after which the beads were separated and the hybridization complexes eluted.

The single-stranded cDNA was converted to double-stranded DNA by incubation for 15 minutes at 70° C. in a final volume of 30 µl containing 2U of Taq polymerase, 20 ng of non-biotinylated probe as primer, and 200 nM of each deoxynucleoside triphosphate. The double-stranded DNA was inserted into a cloning vector (PREP 8, Invitrogen) having an ampicillin resistance marker, and *Escherichia coli* were transformed with 3 µl of the resulting DNA by electroporation at 1800 V, 25 µF, and 100 ohms. The bacteria were plated onto four agar plates containing ampicillin (100 µg/ml). Positive colonies were sequenced by primer walking.

The sequence of one full-length TAP2 clone, 0123, was identical in the 5' untranslated region and in exons 1 through 10 to that of previously characterized TAP2 cDNAs as well as to that of other TAP2 clones (such as clone 0121) isolated from the same library. However, clone 0123 lacked exon 11 and the 3' untranslated region of the other known TAP2 cDNAs and contained a new 27 bp exon (exon 12) and 3' untranslated region. The exon 12 sequence is present in the TAP2 genomic sequence 6533 bp downstream of exon 11. Sequencing of the predicted splice sites confirmed the presence of functional motifs to allow the splicing of exon 10 to exon 11 (clone 0121) and exon 10 to exon 12 (clone 0123). Of the 26 informative cDNAs isolated using the exon 10 probe (SEQ ID NO: 3), 9 corresponded to the new splice form, which was designated TAP2iso.

The predicted TAP2iso protein encoded by TAP2iso contains 653 amino acids, compared with 703 amino acids for the previously characterized TAP2; the COOH-terminal nine residues of TAP2iso are encoded by exon 12. Alignment of amino acid sequence, hydrophobicity and secondary structure were analyzed by GCG program-SEG, MAP, TRANSLATION and PEPPLOT (Genetics Computer Group, Madison, Wis.). All 9 amino acids of TAP2iso encoded by exon 12 are presented and aligned with the first 9 of the 59 residues of TAP2 encoded by exon 11. Hydrophobicity analysis revealed a higher β factor for TAP2iso and in contrast a greater a factor for TAP2.

Vector Construction and Transfection

The TAP1 (TAP1 A allele) cDNA was removed from the pCMV-SPORT vector (Gibco-BRL) by BamHI and SalI digestion and inserted into the PREP 4 vector (Invitrogen) at the BamRI and XhoI sites. TAP2 (clone 0121, TAP2 F allele) and TAP2iso removed from pCMV-SPORT vector by digestion with NotI and KpnI, and inserted into the PREP 8 vector (Invitrogen) at the NotI and KpnI sites.

Plasmid DNAs were prepared using MAXI-PREP kits (Qiagen). TAP1- and TAP2-deficient T2 cells (donated by P. Cresswell, Howard Hughes Medical Institute, Yale University) (1–2×10$^7$ cells/ml) were transfected by electroporation with 10 µg of TAP1 and TAP2 or TAP2iso linear plasmid DNA in a 0.4-cm cuvette at 260 V and 960 µF. Subcloning and selection of transfectants were performed by culturing in the presence of hygromycin (250 µg/ml) or histidinol (2 µM) for the PREP 4 and PREP8 vectors, respectively.

Stable transfectant clones were analyzed by indirect immunofluorescence as previously described (Fu et al., *J. Clin. Invest.*, 91:2301 (1993)) with an anti-HLA class I (A2) murine monoclonal antibody (clone 079 1HA; One Lambda, San Diego, Calif.) and an anti-HLA class II murine monoclonal antibody (clone L243, ATCC accession no. HB55, Rockville, Md.). Immune complexes were detected with fluorescein isothiocyanate-conjugated goat anti-mouse IgG antibodies (Coulter, Hialeah, Fla.) and an Epics Elite flow cytometer (Coulter).

Transport Efficiency of TAP2iso in the Transport of Peptides to the ER

The rate at which MHC class I antigen complexes exit the ER was measured in T2 cells stably transfected with TAP1 and either TAP2 or TAP2iso, as a measure of TAP1/TAP2iso transport efficiency in comparison to TAP1/TAP2. T2 cells were transfected with TAP1 and TAP2iso cDNAs, harvested at 4° C. and cultured for 30 minutes in methionine-free medium. High density cells ($1 \times 10^8$ cells/ml) were labeled for 15 minutes in the presence of 500 μCi [$^{35}$S]methionine (Amersham), and then chased at the indicated times in the presence of 10 mM unlabeled methionine.

Cells were lysed in an ice-cold lysis buffer, and lysates were incubated overnight at 4° C. with protein A Sepharose beads (Pharmacia) and normal rabbit serum (1:200 dilution). The beads were removed by centrifugation and the resulting supernatant was incubated for 12 hours at 4° C. with protein A beads and monoclonal antibody W6/32 (American Type Culture Collection (ATCC) accession no. HB 95), which recognizes HLA class I molecules. The beads were separated by centrifugation and washed extensively, after which proteins were eluted from the beads by boiling for minutes in SDS sample buffer and analyzed by 12.5% of SDS polyacrylamide gel electrophoresis. The gel was treated with enhancer, dried, and exposed to X-ray film for 12 to 72 hours.

Figure 4:
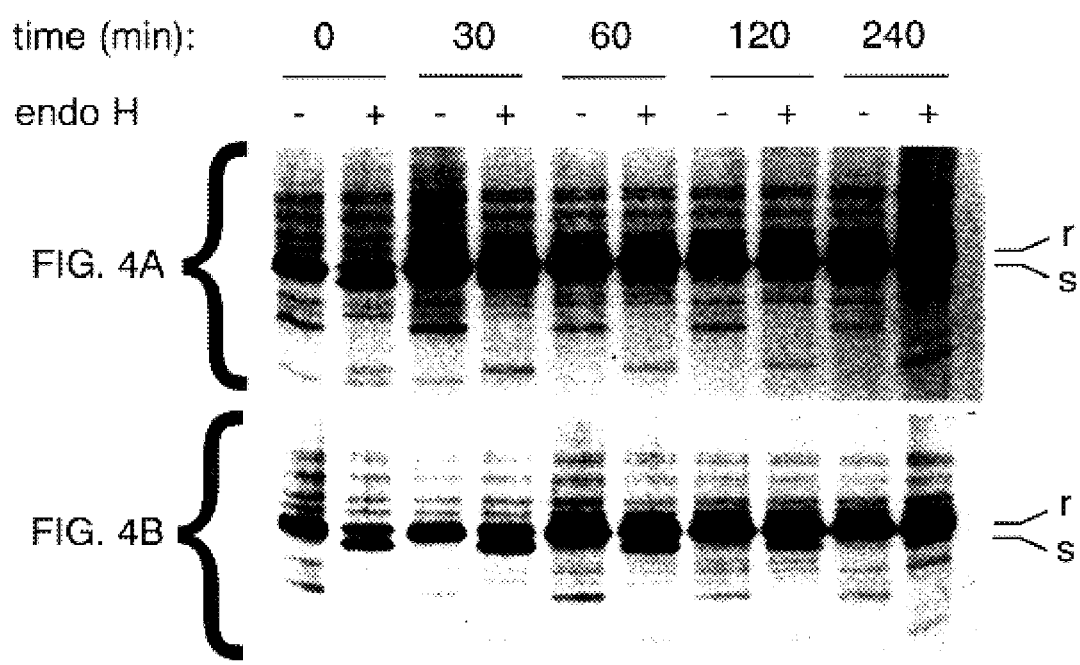
FIGS. 4A and 4B illustrate electrophoresis results showing the effect of TAP2iso together with TAP1 on the maturation of MHC class I molecules in the ER of T2 cells transfected with TAP1 and TAP2iso (FIG. 4A) as compared with untransfected T2 cells (FIG. 4B) incubated in the absence (−) or presence (+) of endoglyosidase H (endo H) at various time points. "r" and "s" indicate class I proteins resistant and sensitive to endo H, respectively. The increased rate of class I maturation in TAP1/TAP2iso-transfected cells is reflected by the difference in endo H sensitivity compared with untransfected cells.

The results are shown in FIGS. 4A and 4B. Samples were incubated in the absence (−) or presence (+) of endo H as previously described (Neefjes et al., *Eur. J. Immunol.*, 25:1133 (1995)). "r" and "s" indicate HLR class I proteins resistant and sensitive to endo H, respectively. The results reveal that TAP2iso (FIG. 4A) and TAP2 (data not shown) both expressed with TAP1 showed increasing HLA class I maturation as reflected in decreasing endo H sensitivity to similar extents relative to that apparent in untransfected T2 cells (FIG. 4B).

Peptide Selectivity of TAP2iso in the Transport of Peptides to the ER

The peptide selectivities of TAP1/TAP2 and TAP1/TAP2iso heterodimers were compared by measuring the transport of $^{125}$I-labeled peptides into the ER of transfected T2 cells permeabilized with streptolysin O. Peptides that have entered the ER were detected on the basis of their consequent glycosylation.

The transport of three different peptides was measured: Test Peptide RRYQNSTEL (SEQ ID NO: 6), which is a variant of a peptide eluted from HLA class I B27 (Androlewicz et al., *Proc. Natl. Acad. Sci. U.S.A.*, 91:12716 (1994)), with a polar asparagine substitute for a charged lysine at position 5 to produce an NXT motif for glycosylation; Test Peptide IYLGPFSPNVTL (SEQ ID NO: 7); and Test Peptide TVDNKTRYE (SEQ ID NO: 8), which is transported efficiently by the product of the rat TAP2$^a$ allele but poorly by that of the rat TAP2$^u$ allele (Momburg et al., *Nature*, 367:648 (1994); Fu et al., *J. Clin. Invest.*, 91:2301 (1993); Ortmann et al., *Nature*, 368:864 (1994)). The size of all test peptides fell within the range of 8–12 amino acids that is optimal for transport by all TAP proteins characterized to date.

The test peptides were synthesized by Quality Controlled Biochemical, Inc. (Hopkington, Mass.), and their sequences were confirmed by mass spectrometry. The purity of peptide preparations was >95% as judged by high-performance liquid chromatography. 10 mM stock solutions of peptides were prepared in dimethyl sulfoxide. Peptides (25 μg) were directly iodinated at unique tyrosine residues with the use of chloramine T (Sigma, St. Louis, Mo.), and free iodine was removed by gel filtration using Sephadex G 10 (Pharmacia) column chromatography. The specific activity of the $^{125}$I-iodinated peptides ranged from 20 to 50 cpm/fmol.

Glycosylated $^{125}$I Peptide RRYQNSTEL (SEQ ID NO: 6), Peptide IYLGPFSPNVTL (SEQ ID NO: 7), or Peptide TVDNKTRYE (SEQ ID NO: 8) was recovered and measured. The peptide translocation assay was performed essentially as previously described (Neefjes et al., *Science*, 261:769 (1993); and Momburg et al., *J. Exp. Med.*, 179:1613 (1994)). Briefly, $2.5–5.0 \times 10^6$ T2 cell (transfected or untransfected) were washed once with incubation buffer (130 mM KCl, 10 mM NaCl, 1 mM CaC$_2$, 2 mM EDTA, 2 mM MgCl$_2$, 5 mM Hepes, pH 7.3) and permeabilized for 10 minutes at 37° C. with streptolysin O (2 IU/ml) (Wellcome, Beckenham, UK) in 50 μl of incubation buffer. After further addition of 10 μl of 100 mM adenosine triphosphate, 10 μl of $^{125}$I-labeled peptide (~15 pM), and 30 μl of incubation buffer, cells were incubated for an additional 10 minutes at 37° C. Transport was terminated by the addition of 1 ml of 1% NP-40 detergent, after which nuclei were removed by centrifugation and glycosylated peptides were recovered using concanavalin A-Sepharose (Sigma, St. Louis, Mo.) and quantitated with a gamma counter (LKB-Wallac).

Figure 5:
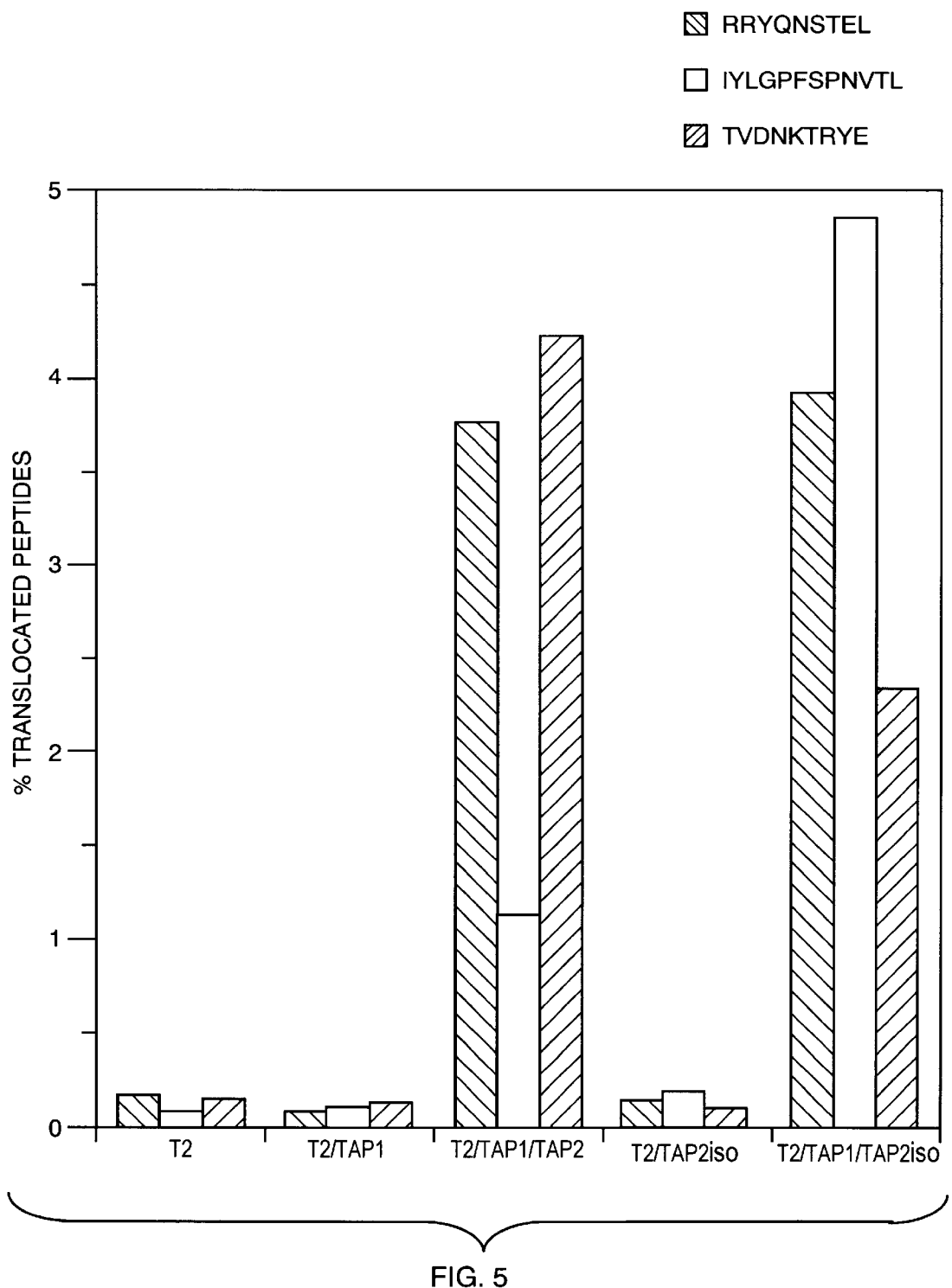
FIG. 5 illustrates peptide selectivity of TAP1/TAP2 and TAP1/TAP2iso heterodimers in permeabilized T2 transfectants. Three different glycosylated and radiolabeled ($^{125}I$) peptides, RRYQNSTEL (SEQ ID NO: 6), IYLGPFSPNVTL (SEQ ID NO: 7) and TVDNKTRYE (SEQ ID NO: 8) were recovered and measured. The data presented are means of three separate experiments employing ten different sets of transfectants. The amount of translocated peptide is shown as a percentage of the total amount of radiolabeled peptide introduced. The results demonstrate that RRYQNSTEL was translocated with equal efficiency by TAP1/TAP2 or TAP1/TAP2iso heterodimers, but that IYLGPFSPNVTL was transported four times more efficiently by the TAP1/TAP2iso heterodimer compared to the TAP1/TAP2 transporter, and that TVDNKTRYE was transported more efficiently in the TAP1/TAP2 transfectant.

The results are shown in FIG. 5 as means±SD of 3 independent experiments with 10 different clones. Peptide RRYQNSTEL was transported to similar extents by TAP1/TAP2 and TAP1/TAP2iso, while Peptide TVDNKTRYE was transported to a greater extent by TAP1/TAP2 than by TAP1/TAP2iso, and Peptide IYLGPFSPNVTL was transported to a greater extent by TAP/TAP2iso than by TAP1/TAP2. The amount of translocated peptide is shown as the percentage of the input radioactive peptide. Untransfected T2 cells or those expressing TAP1 or TAP2iso alone did not show appreciable transport of any test peptide.

Differential peptide selectivity of the TAP1/TAP2 and TAP1/TAP2iso heterodimers was further investigated by competition experiments with $^{125}$I-labeled Peptide RRYQNSTEL (SEQ ID NO: 6) and various unlabeled peptides: Peptide RRYQNSTEL (SEQ ID NO: 6); Peptide IYLGPFSPNVTL (SEQ ID NO: 7); Peptide TVDNKTRYE (SEQ ID NO: 8); Peptide SYSMEHGRWGKPVGKKRRPVKVYP (SEQ ID NO: 9), the S1–24 fragment of human adrenocorticotropic hormone); and Peptide RGFFYTPKA (SEQ ID NO: 10), residues 22 to 30 (human insulin B chain). The iodinated 9-mer Peptide RRYQNSTEL was translocated in the presence of different concentrations of unlabeled competition peptides. The glycosylated peptides were recovered by Con A-Sepharose and quantitated. FIGS. 6A–6E graphically illustrate the results of: (6A) competition of $^{125}$I-Peptide RRYQNSTEL with unlabeled Peptide RRYQNSTEL (self); (6B) competition of $^{125}$I-Peptide RRYQNSTEL with Peptide IYLGPFSPNVTL; (6C) competition of $^{125}$I-Peptide RRYQNSTEL with Peptide TVDNKTRYE; and (6D) competition of $^{125}$I-Peptide RRYQNSTEL with Peptide SYSMEHGRWGK-PVGKKRRPVKVYP; and (6E) competition of $^{125}$I-Peptide RRYQNSTEL with Peptide RGFFYTPKA.

Figure 6A:
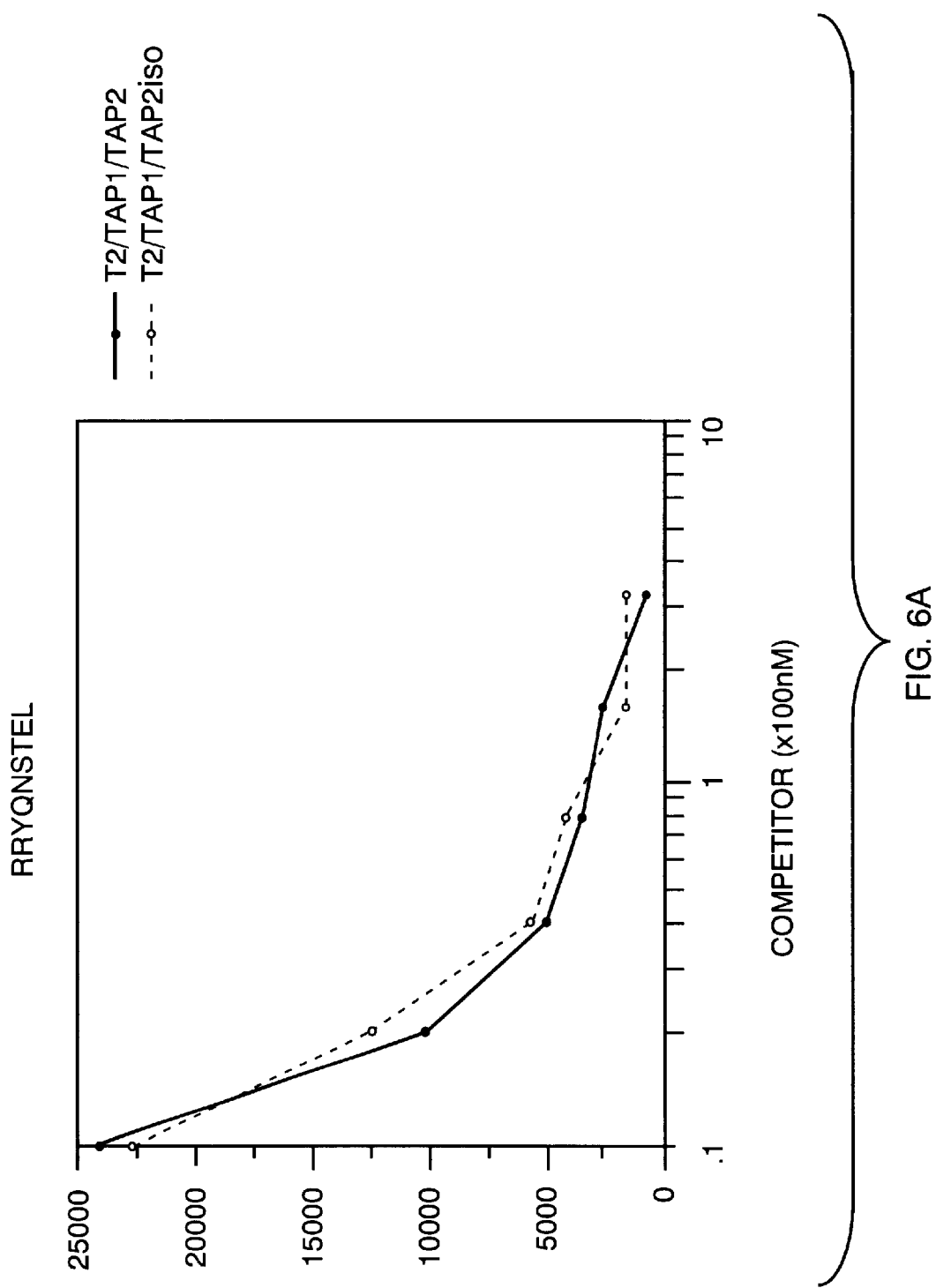
FIGS. 6A, 6B, 6C, 6D and 6E illustrate competitive transport efficiency in transfected T2 cells. The peptide RRYQNSTEL (SEQ ID NO: 6) is analyzed for transport efficiency in competition with itself (FIG. 6A), in competition with IYLGPFSPNVTL (SEQ ID NO: 7) (FIG. 6B), in competition with TVDNKTRYE (SEQ ID NO: 8) (FIG. 6C), in competition with SYSMEHGRWGK-PVGKKRRPVKVYP (SEQ ID NO: 9) (FIG. 6D), and in competition with RGFFYTPKA (SEQ ID NO: 10).
Figure 6B:
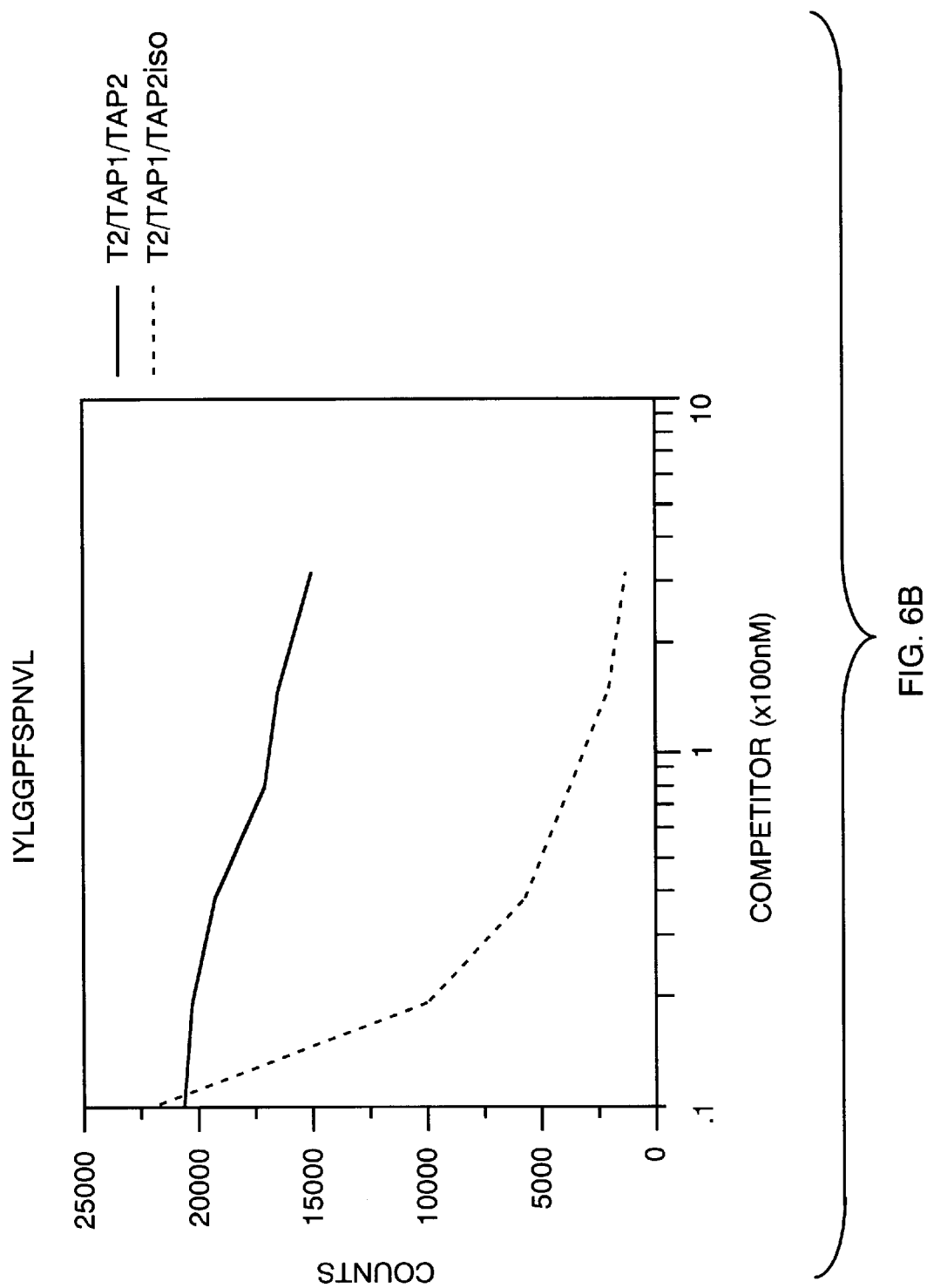
Figure 6C:
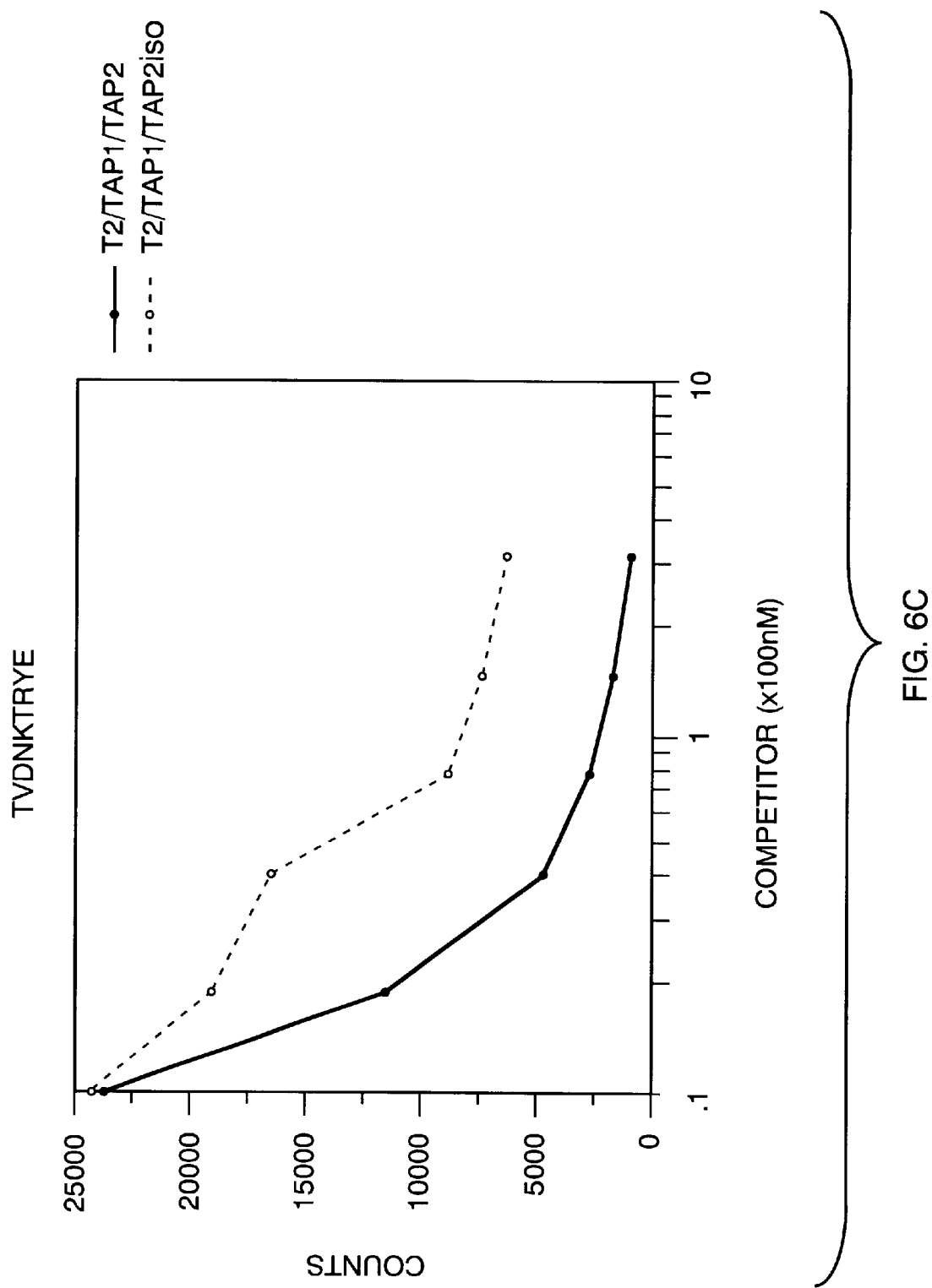
Figure 6D:
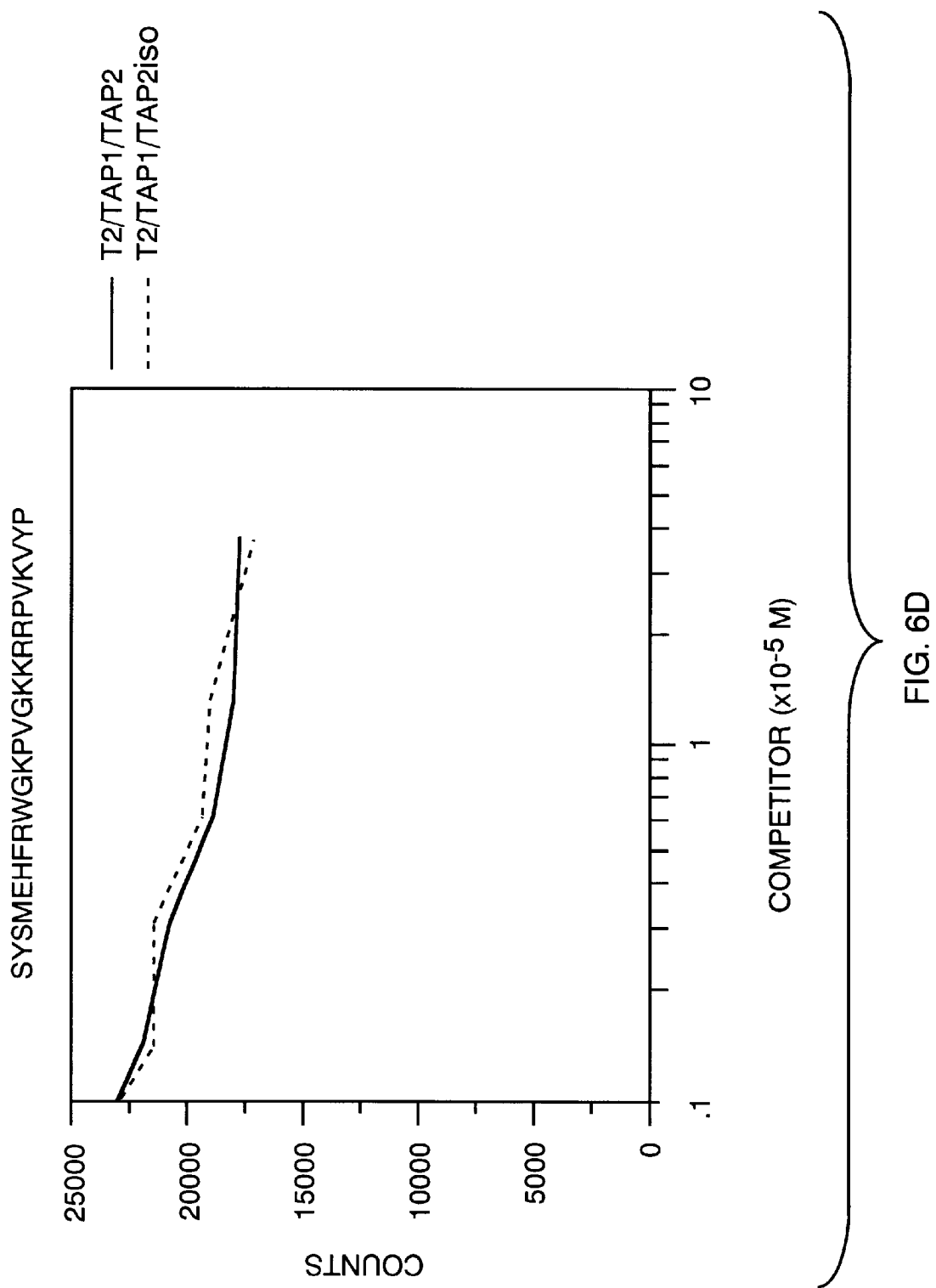
Figure 6E:
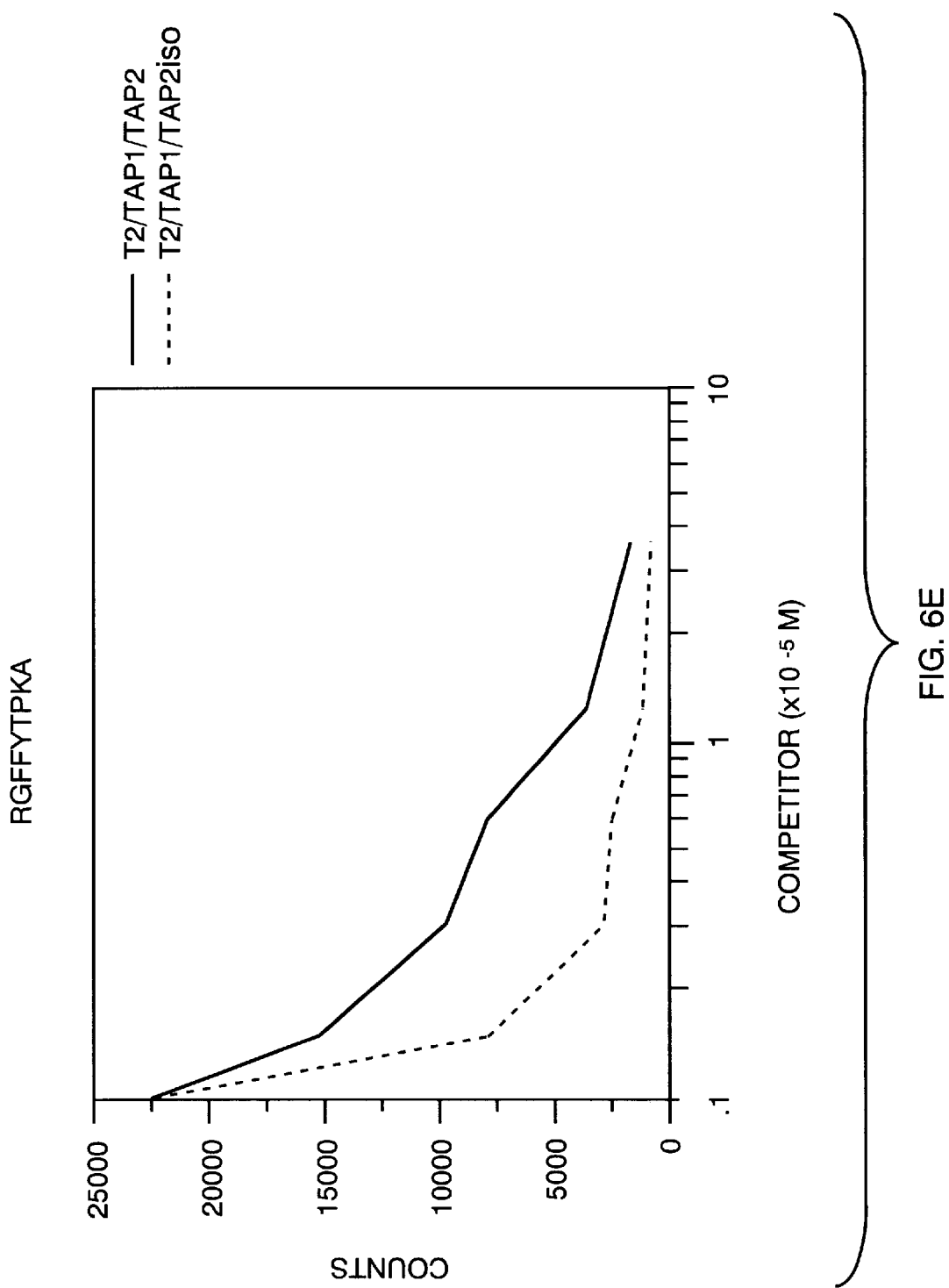

Unlabeled Peptide RRYQNSTEL inhibited transport of $^{125}$I-labeled Peptide RRYQNSTEL in TAP1/TAP2 and TAP1–TAP2iso transfectants to similar extents; the median inhibitory concentration (IC$_{50}$) was ~0.15 μM in both instances (FIG. 6A). With unlabeled Peptide IYLGGPFSP-NVL as competitor, transport of $^{125}$I-Peptide RRYQNSTEL was inhibited to a markedly greater extent in TAP1/TAP2iso transfectants than in TAP1/TAP2 transfected cells (FIG. 6B). With unlabeled Peptide TVDNKTRYE as competitor, transport of $^{125}$I-Peptide RRYQNSTEL was inhibited to a markedly greater extent in TAP1/TAP2 transfectants than in TAP1/TAP2iso transfected cells (FIG. 6C). Peptide SYSMEHGRWGKPVGKKRRPVKVYP, a 24-residue peptide, did not inhibit transport of Peptide RRYQNSTEL in either transfectant to a substantial extent (FIG. 6D), which is consistent with previous studies of TAP transporters showing a preference for peptides of 8 to 12 amino acids. Finally, Peptide RGFFYTPKA inhibited the transport of Peptide RRYQNSTEL in TAP1/TAP2iso to a greater extent than that mediated by TAP1/TAP2 (IC$_{50}$ values of 0.11 and 0.3 μM, respectively) (FIG. 6E). Thus, the two transporter heterodimers showed opposite preferences with regard to three of the five test peptides.

TAP2iso Restoration of MHC Class I Antigen Complex Surface Presentation in T2 Cells The introduction of TAP1 and TAP2 genes into mutant T2 cells has been shown to restore the normal processing and surface expression of HLA class I molecules (Attaya et al., Nature, 355:647 (1992); Spies and DeMars, Nature, 351:323 (1991); and Powis et al., J. Exp. Med., 173:913 (1991)). The effects on surface HLA class I antigen complex expression was investigated to compare the functional properties of TAP2 and TAP2iso.

T2 cells were transfected with TAP1 cDNA in combination with TAP2 or TAPiso cDNAs as described above. The surface expression of MHC class I molecule A2 and the and MHC class II epitope recognized by monoclonal antibodies 0791HA and L243, respectively, were examined by flow cytometry in T1 cells or T2 cells transfected with TAP1 and either TAP2 or TAP2iso cDNAs.

Figure 7:
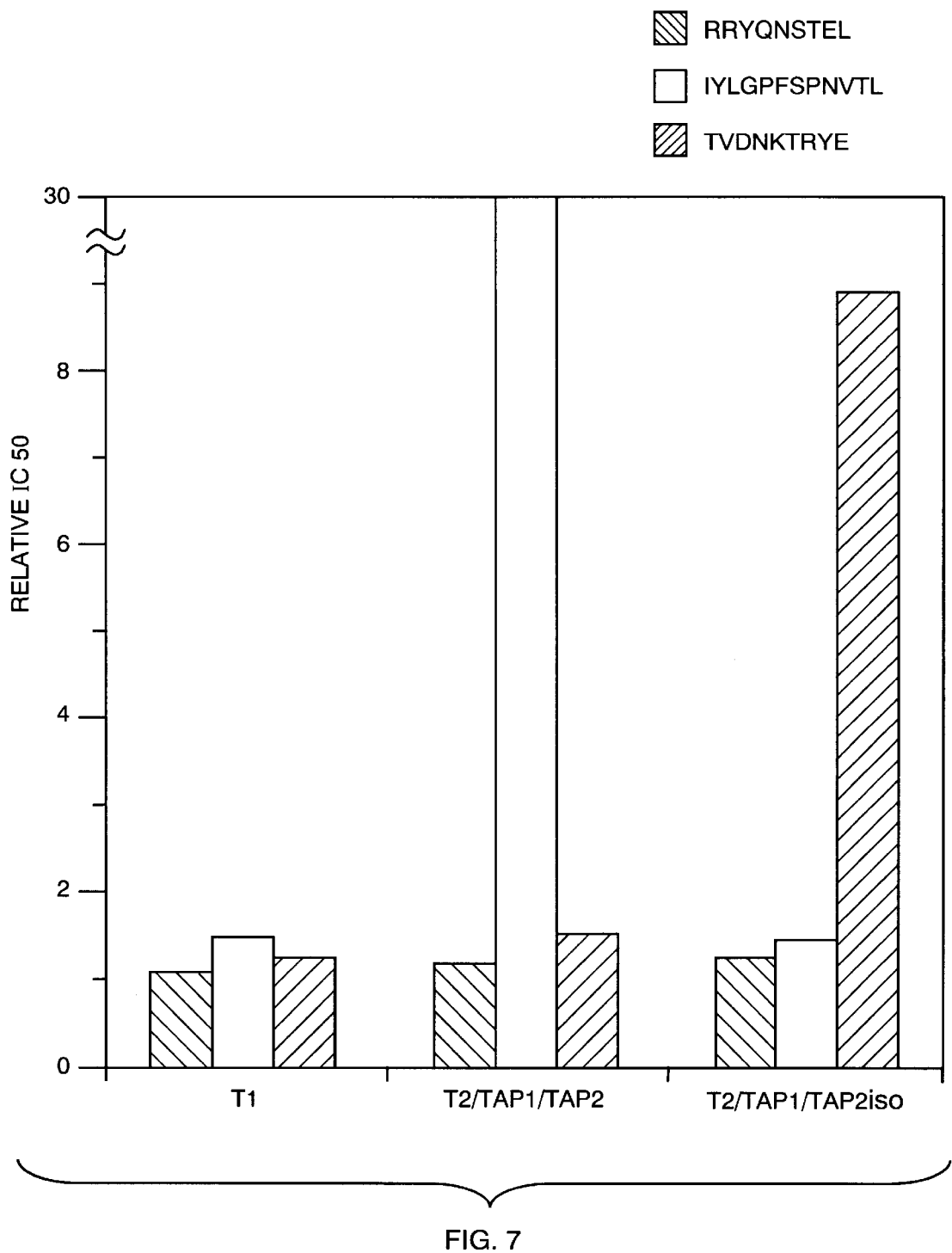
FIG. 7 compares relative fifty percent inhibitory concentrations (IC50) of the test peptides (RRYQNSTEL, IYLGPFSPNVTL, and TVDNKTRYE) in T1 cells (which naturally co-express both TAP2 and TAP2iso) and T2 transfectants expressing either TAP1/TAP2 or TAP1/TAP2iso. The T1 cells show transportation of all the test peptides with equal efficiency, whereas the transfectants exhibit preferential transport of one of the three test peptides in comparison to RRYQNSTEL.

Flow cytometric analysis revealed that transfection of T2 cells with TAP1 or TAP2iso cDNAs alone had no effect on surface expression of HLA class I (see Table 1, below). In contrast, transfection of T2 cells with TAP1 and TAP2 or TAP1 and TAP2iso cDNA combinations resulted in restored surface expression of MHC class I. Surface MHC class I expression was 30% greater in cells transfected with TAP1–TAP2iso cDNAs than in those transfected with TAP1–TAP2 cDNAs. Consistent with the fact that T2 cells have a large homozygous deletion that encompasses both TAP and MHC II genes, only parental T1 cells were stained with antibodies to human MHC class II (FIG. 7).

TABLE 1

Restoration of surface expression of HLA class I (A2) on T2 cells transfected with both TAP1 and either TAP2 or TAP2iso cDNAs.

| Cell Line | mRNA | | | Mean fluorescence of HLA class 1 (A2)* |
|---|---|---|---|---|
| | TAP1 | TAP2 | TAP2iso | Mean ± SD |
| T1 | (+) | (+) | (+) | 8.43 ± .21 |
| T2 | | | | 5.26 ± .20 |
| T2 (TAP1/2iso) | (+) | | (+) | 11.16 ± .50† |
| T2 (TAP1/2) | (+) | (+) | | 7.59 ± .31 |
| T2 (TAP2) | | | (+) | 6.11 ± 1.09 |
| T2 (TAP1) | (+) | | | 5.19 ± .35 |

*Data are means ± SD for four separate experiments performed over a 6-month period with at least three stable clones for each transfection group.
†$P < 0.001$ vs. T2 cells transfected with TAP1 and TAP2 cDNAs.

TAP2iso Expression in Various Human Cell Lines

Reverse transcription polymerase chain reaction (RT-PCR) analysis and sequencing of the RT-PCR products was conducted to determine the presence of TAP2iso expression in various human cell lines.

RT-PCR was performed with total RNA prepared from the various cell lines with Trizol reagent (Gibco-BRL). For the TAP2 and TAP2iso cDNAs, PCR was performed with a shared primer targeted to exon 10 (SEQ ID NO: 3) and two different antisense primers targeted to exon 11 (SEQ ID NO: 11) and exon 12 (SEQ ID NO: 12), respectively. β$_2$-microglobulin RNA was amplified for a RT-PCR control, and the primers used are shown at SEQ ID NO: 13 and SEQ ID NO: 14.

First strand cDNA was synthesized from 3 μg of RNA by incubation at 42° C. for 50 minutes in a final volume of 50 μl containing 200 U of Superscript II reverse transcriptase (Gibco-BRL), 0.05 μg of oligo (dT), and 200 nM of each deoxynucleoside triphosphate. A portion (1.5 to 3.0 μl) of the reaction mixture was then subjected to PCR in a final volume of 50 μl containing 0.1 nM of each primer, 200 nM of each deoxynucleoside triphosphate, and 2.5 U of Taq polymerase. After an initial denaturation step of 94° C. for 2 minutes, amplification was performed for 36 cycles of 94° C. for 30 sec., 57° C. for 30 sec. and 72° C. for 1 min. PCR products were analyzed by agarose gel electrophoresis and sequenced using DNA polymeras (Sequenase 2.0, Amersham Life Science, Arlington Height, Ill.).

Results are shown in FIG. 3. RT-PCR analysis revealed the presence of both TAP2 and TAP2iso mRNAs in human fresh peripheral blood lymphocytes (lanes 3 and 4), Epstein-Barr virus-immortalized B cell lines (lanes 5 and 6), MOLT-4 acute lymphoblastic leukemia cells (lane 7), THP-1 monocytic cells (lane 8), U-937 histocytic lymphoma cells (lane 9), HeLa epithelioid carcinoma cells (lane 10), and PACA pancreatic carcinoma cells (lane 11). The presence of TAP2 and TAP2iso mRNAs in T1 cells, a human lymphoblastoid B cell line (lane 1), but not in T1-derived T2 cells (lane 2), which contain a large homozygous deletion of the HLA class II region that encompasses the TAP1 and 2 genes, confirmed the specificity of the RT-PCR and was also consistent with TAP2iso mRNA being a splice product of TAP2 rather than being derived from a distinct gene located elsewhere in the genome.

EXAMPLE 2
Detection of TAP1iso and TAP1iso$^2$

Multiple samples of cDNA were analyzed using PCR primers designed using genomic sequence information of the DNA linking the coding regions of the 3' exons known for TAP1 DNA, i.e., exons 9, 10 and 11 (and the introns), two PCR primers were designed. The forward primer (from exon 9) was: 5'-TAGTTTCATCTCTGGACTCCCTCA-3' (SEQ ID NO: 20); the reverse primer (from the intron following exon 10) was: 5'-AGGTGTCTTTGCCTCGTCTTCT-3' (SEQ ID NO: 21). Total RNA, mRNA and cDNA samples were prepared from various cell lines. First strand cDNAs were synthesized from 3 μg of RNA or 0.5 μg of mRNA by incubating at 42° C. for 50 min. in a final volume of 50 μl. A portion of the reaction mixture was then subjected to PCR with the above set of primers. PCR products were then analyzed by agarose gel electrophoresis, and some samples were recovered for DNA sequencing. Analysis of the PCR products revealed the presence of two unexpected PCR products not corresponding to the expected TAP1 product but present in all human cell samples tested. This indicated two additional splice variants corresponding to TAP1, and these were designated TAP1iso and TAP1iso$^2$. The fact that the two variants appeared in all samples indicated that the variants were not allelic polymorphs but were variants of the original gene.

Figure 8:
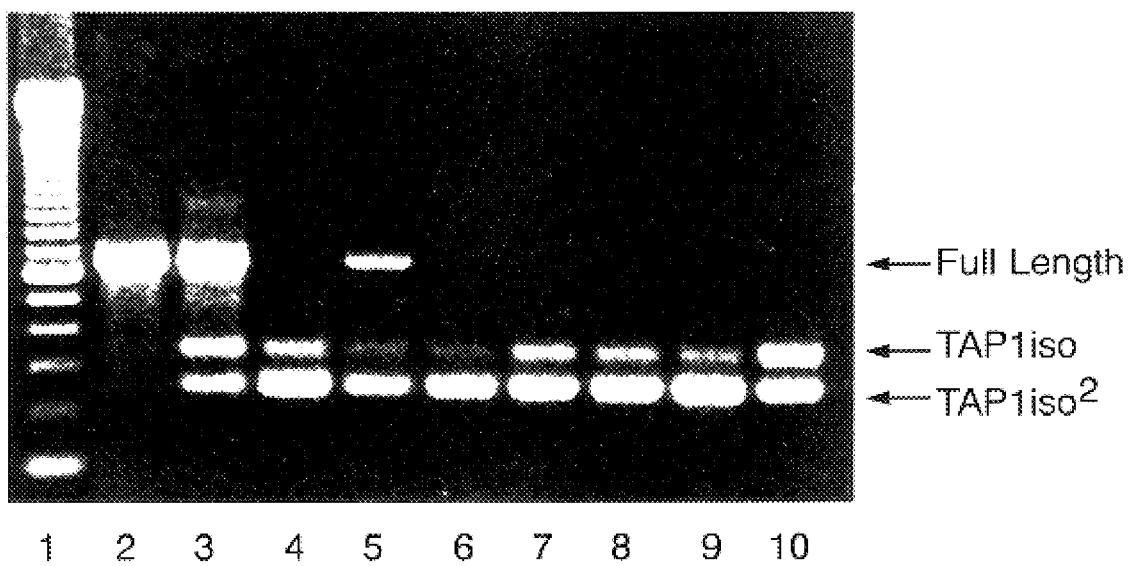
FIG. 8 illustrates electrophoresis results showing co-transcription of TAP1iso and TAP1iso$^2$ mRNAs in EBV-stabilized cells from various human subjects. Lanes: (1) DNA molecular size markers; (2) genomic DNA from a first individual (Control #1); (3) nuclear RNA from Control #1; (4) cytoplasmic mRNA from Control #1; (5) total RNA from Control #1, without DNAase digestion; (6) total RNA from Control #1, with DNAase digestion; (7) cytoplasmic mRNA from a second individual (Control #2), with DNAase digestion; (8) cytoplasmic mRNA from a third individual (Control #3), with DNAase digestion; (9) cytoplasmic mRNA from a fourth individual (Control #4), with DNAase digestion; (10) cytoplasmic mRNA from a diabetic patient, with DNAase digestion.

Referring to FIG. 8, results of electrophoresis of the RT-PCR products from various samples using the above primers are shown. Lane 1 shows molecular weight markers; lane 2 shows PCR products from genomic DNA of and EBV-immortalized B cell line from a first individual (Control #1); lane 3 shows RT-PCR products from nuclear mRNA from the same Control #1 cell line; lane 4 shows RT-PCR products from cytoplasmic mRNA from Control #1; lane 5 shows RT-PCR products from total RNA from Control #1, without DNAase; lane 6 shows RT-PCR products from total RNA from Control #1, with DNAase digestion; lane 7 shows RT-PCR products from cytoplasmic mRNA of an EBV-immortalized B cell line from a second individual (Control #2), with DNAase digestion; lane 8 shows RT-PCR products from cytoplasmic mRNA of an EBV-immortalized B cell line from a third individual (Control #3), with DNAase digestion; lane 9 shows RT-PCR products from cytoplasmic mRNA of an EBV-immortalized B cell line from a fourth individual (Control #4), with DNAase digestion; and lane 10 shows RT-PCR products from cytoplasmic mRNA of an EBV-immortalized B cell line from a patient with type I diabetes.

As can be seen in the figure, the high molecular weight PCR product amplifying the entire sequence spanning the intron between exons 9 and 10 is clearly visible in samples including genomic DNA or unspliced RNA (lanes 2, 3 and 5). Cytoplasmic and nuclear mRNA are compared (e.g., lanes 3 and 4) to confirm that the unexpected products are not amplified mRNA that has not been completely spliced. Comparison of cytoplasmic mRNA from several individuals (e.g., lanes 4 and 6–10) confirms that the TAP1iso and TAP1iso2 products are splice variants and not random mutations. The relative intensities of the signals is intriguing, in that it suggests that expression ratios may differ to some extent from individual to individual, and the equal, intense bands shown in the diabetic subject (lane 10) suggest a possible link between TAP1 isoform expression and the disease, although further investigation would be necessary to confirm such an association.

Figure 9B:
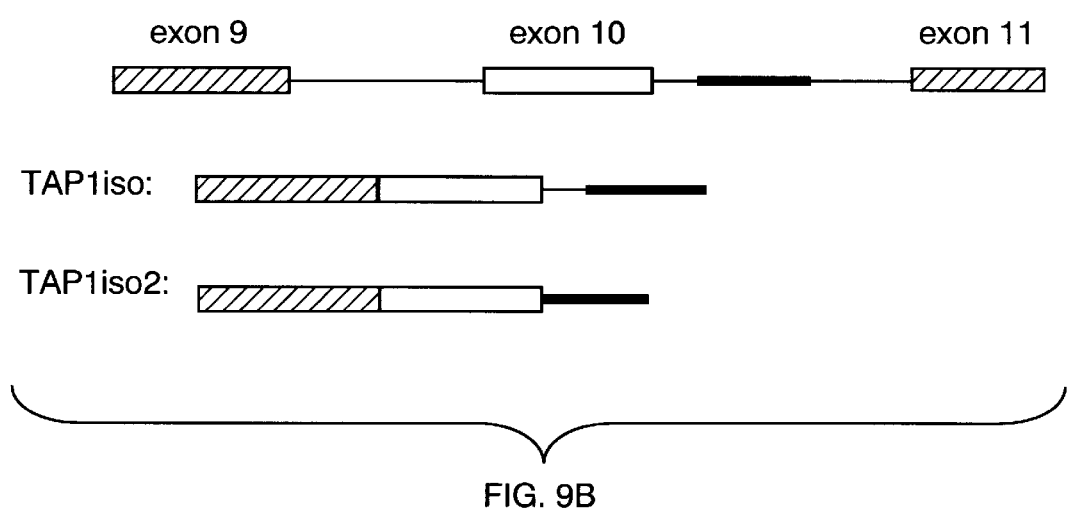

Sequencing of the TAP1iso and TAP1iso$^2$ bands showed that TAP1iso represented a splice form containing exon 9, exon 10 and retaining intron 10 at least to the primer location, and that TAP1iso2 contained both exons 9 and 10 but a smaller portion of retained intron 10. A comparison of the PCR products is shown in FIG. 9A. A schematic of the relationship between genomic DNA and the DNA indicated by the PCR products is shown in FIG. 9B. The heavy-lined area of intron 10 indicates the section of the intron common to both splice variant PCR products, up to the primer boundary.

EXAMPLE 3
Detection of TAP2iso$^2$

Using methods similar to those described above, cDNA derived from cytoplasmic mRNA of PBLs from multiple human donors was amplified and analyzed by gel electrophoresis to determine whether additional TAP2 splice variants could be detected using two exonic primers. The forward primer was: 5'-GCTACTAGTGCCTAGATGTGCAGT-3' (SEQ ID NO: 22), located in TAP2 exon 10; and the reverse primer was: 5'-CTTCTGCAGCTTGCCCTCCTGGAG-3' (SEQ ID NO: 23), located in TAP2 exon 11.

Figure 10:
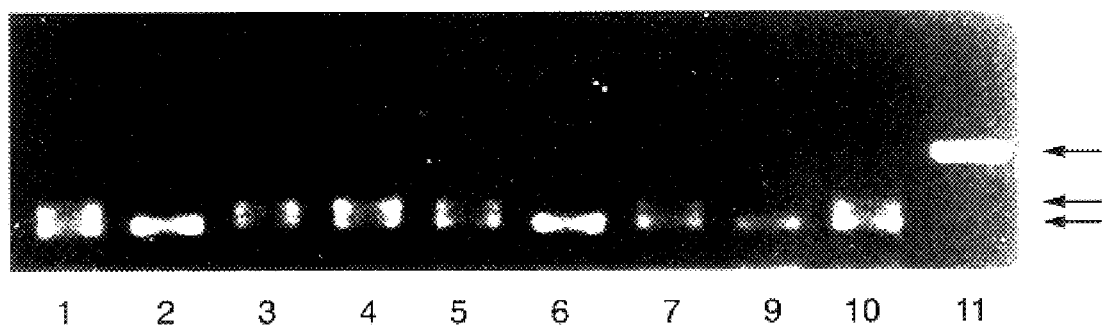
FIG. 10 illustrates electrophoresis results showing co-transcription in several individuals of a fully spliced TAP2 and a variant in some individuals presumably retaining part of intron 10. The second product indicates a further TAP2 splice variant, designated TAP2iso$^2$. All lanes show PCR products of cDNA derived from cytoplasmic mRNA from fresh peripheral blood lymphocytes (PBLs) from several normal and one hypothyroid individual. Lanes: (I) Control (normal) individual 1; (2) Control individual 2; (3) hypothyroid patient; (4) Control individual 3; (5) Control individual 4; (6) Control individual 5; (7) Control individual 6; (9) Control individual 7; (10) Control individual 8; (11) control genomic DNA sample.

Analysis of the PCR products showed that PBLs of all of the donors exhibited the fully spliced TAP2 message (lower arrow, FIG. 10) but that some donors also exhibited a larger product (middle arrow, FIG. 10) with presumed partial retention of intron 10 sequence. This second product indicated a second TAP2 splice variant, which included at least portions of exons 10 and 11 and a portion of intron 10, was designated TAP2iso$^2$. The control genomic DNA sample (lane 11, upper arrow) showed an expected very large molecular weight PCR product including amplified DNA that is present in neither of the TAP2 splice variants. Referring to FIG. 10, lane 1 shows the PCR products derived from cytoplasmic mRNA from a first individual; lane 2 shows the PCR products derived from cytoplasmic mRNA from a second individual; lane 3 shows the PCR products derived from cytoplasmic mRNA from a hypothyroid patient; lane 4 shows the PCR products derived from cytoplasmic mRNA from a third individual; lane 5 shows the PCR products derived from cytoplasmic mRNA from a fourth individual; lane 6 shows the PCR products derived from cytoplasmic mRNA from a fifth individual; lane 7 shows the PCR products derived from cytoplasmic mRNA from a sixth individual; lane 9 shows the PCR products derived from cytoplasmic mRNA from a seventh individual; and lane 10 shows the PCR product derived from a genomic DNA sample. The bands corresponding to the TAP2iso2 product are not present in three of the normal individuals (lanes 2, 6 and 9); and the hypothyroid patient does not show any readily descernable abnormality associated with the expression of these two TAP2 isoforms.

By following the examples given above, it is contemplated that additional splice variants of the TAP1 and TAP2 proteins will be discovered and that their specificities for different types and repertoires of antigen peptides will be mapped out. The discovery of multiple splice variants having similar but not identical transport functionality expands previous views as to the limits of antigen display by MHC class I molecules. The mechanism by which cytotoxic T cells are alerted to somatic events requiring an immune response is now seen to be more complex than originally thought, and new methods for detecting predisposition to genetically linked autoimmune disorders can now be contemplated. For example, in a disease that is characterized by a deletion or a mutation preventing expression of one or more of the TAP splice variants, gene therapy to replace expression of the lost splice variant(s), or other therapy to restore surface expression of the peptide repertoire for which the lost splice variant is specific, will effectively treat the disease. Similarly, a virus that knocks out expression of a splice variant or alters the ratio of expression of two or more splice variants, may be diagnosed by detection of the change in splice variant expression and may be combatted using vaccines designed to overcome the reduction or elimination of the MHC class I antigen complexes that results from the virus-mediated changes in splice variant expression. Some tumors may also arise through alteration of splice variant expression, and thus certain cancers may be diagnosed by detecting altered splice variant expression and treated by correcting the expression or otherwise overcoming the change in MHC class I antigen complex display that results from the altered expression. These and other obvious applications of the discoveries hereing relating to TAP splice variants are contemplated and are intended to be included in the scope of the present invention.

Table of Sequence Identification Numbers (SEQ ID NOS:)

| SEQ ID NO: | Description |
|---|---|
| 1 | Amino acid sequence of TAP2iso exon 12 polypeptide |
| 2 | Amino acid sequence of TAP2iso polypeptide |
| 3 | TAP2 exon 10 oligo probe |
| 4 | Nucleic acid sequence of *TAP2iso* |
| 5 | Nucleic acid sequence of *TAP2iso* exon 12 |
| 6 | Test Peptide RRYQNSTEL |
| 7 | Test Peptide IYLGPFSPNVTL |
| 8 | Test Peptide TVDNKTRYE |
| 9 | Test Peptide SYSMEHGRWGKPVGKKRRPVKVYP |
| 10 | insulin β chain$_{22-30}$: RGFFYTPKA |
| 11 | TAP2 exon 11 oligo probe |
| 12 | TAP2 exon 12 oligo probe |
| 13 | β$_2$-microblobulin oligo probe |
| 14 | β$_2$-microblobulin oligo probe |
| 15 | Amino acid sequence of TAP2 polypeptide |
| 16 | Amino acid sequence of TAP2 exon 11 polypeptide |
| 17 | Nucleic acid sequence of *TAP2* |
| 18 | Nucleic acid sequence of *TAP1* |
| 19 | Amino acid sequence of TAP1 polypeptide |
| 20 | Nucleic acid sequence of TAP1 exon 9 primer |
| 21 | Nucleic acid sequence of TAP1 intron 10 primer |
| 22 | Nucleic acid sequence of TAP2 exon 10 primer |
| 23 | Nucleic acid sequence of TAP2 exon 11 primer |

All for the publications cited herein are hereby incorporated by reference in their entirety.

What is claimed is:

1. An isolated nucleic acid comprising a polynucleotide sequence that encodes a TAP2 splice variant having the amino acid sequence of SEQ ID NO: 2, or a complementary polynucleotide sequence thereof.

2. An expression vector comprising the nucleic acid of claim 1.

3. A host cell transfected with the vector according to claim 2.

4. A process for producing a polypeptide comprising culturing the host cell of claim 3 under conditions suitable to produce the polypeptide encoded by said nucleic acid.

5. An isolated nucleic acid encoding a TAP2 exon 12 polypeptide.

6. An expression vector comprising the nucleic acid of claim 5.

7. A host cell transfected with the vector according to claim 5.

8. A process for producing a polypeptide comprising culturing the host cell of claim 7 under conditions suitable to produce the polypeptide encoded by said nucleic acid.

9. The isolated nucleic acid of claim 5, wherein said nucleic acid has the sequence of SEQ ID NO: 5.

10. An expression vector comprising the nucleic acid of claim 9.

11. A host cell transfected with the vector according to claim 10.

12. A process for producing a polypeptide comprising culturing the host cell of claim 11 under conditions suitable to produce the polypeptide encoded by said nucleic acid.

* * * * *